(12) United States Patent
Lo et al.

(10) Patent No.: US 11,512,306 B2
(45) Date of Patent: Nov. 29, 2022

(54) GESTATIONAL AGE ASSESSMENT BY METHYLATION AND SIZE PROFILING OF MATERNAL PLASMA DNA

(71) Applicant: The Chinese University of Hong Kong, Shatin (CN)

(72) Inventors: Yuk-Ming Dennis Lo, Kowloon (CN); Rossa Wai Kwun Chiu, Shatin (CN); Kwan Chee Chan, Shatin (CN); Peiyong Jiang, Shatin (CN)

(73) Assignee: The Chinese University of Hong Kong, Shatin (HK)

( * ) Notice: Subject to any disclaimer, the term of this patent is extended or adjusted under 35 U.S.C. 154(b) by 294 days.

(21) Appl. No.: 15/787,050

(22) Filed: Oct. 18, 2017

(65) Prior Publication Data

US 2018/0105807 A1 Apr. 19, 2018

Related U.S. Application Data

(60) Provisional application No. 62/410,108, filed on Oct. 19, 2016.

(51) Int. Cl.
| | | |
|---|---|---|
| *C12N 15/10* | (2006.01) | |
| *C12Q 1/6888* | (2018.01) | |
| *C12Q 1/6858* | (2018.01) | |
| *G01N 33/53* | (2006.01) | |

(52) U.S. Cl.
CPC ....... *C12N 15/1003* (2013.01); *C12Q 1/6858* (2013.01); *C12Q 1/6888* (2013.01); *C12Q 2600/154* (2013.01); *G01N 33/53* (2013.01)

(58) Field of Classification Search
CPC C12N 15/1003; C12Q 1/6858; C12Q 1/6888; C12Q 2600/154; G01N 33/53
See application file for complete search history.

(56) References Cited

U.S. PATENT DOCUMENTS

| | | |
|---|---|---|
| 8,620,593 B2 | 12/2013 | Lo et al. |
| 9,732,390 B2 | 8/2017 | Lo et al. |
| 9,892,230 B2 | 2/2018 | Lo et al. |
| 2012/0277119 A1 | 11/2012 | Ehrich et al. |
| 2014/0080715 A1* | 3/2014 | Lo .......... C12Q 1/6809 506/2 |
| 2016/0217251 A1 | 7/2016 | Lo et al. |

FOREIGN PATENT DOCUMENTS

| | | |
|---|---|---|
| CN | 102648292 A | 8/2012 |
| CN | 104254618 A | 12/2014 |
| CN | 104781422 A | 7/2015 |
| WO | 2013132305 A1 | 9/2013 |
| WO | WO-2014043763 A1 * | 3/2014 ..... C12Q 1/6886 |

OTHER PUBLICATIONS

Bohlin et al., Prediction of gestational age based on genome-wide differentially methylated regions, Oct. 7, 2016, Genome Biology, 17:207, p. 1-9 (Year: 2016).*
Knight et al., An epigenetic clock for gestational age at birth based on blood methylation data, Oct. 7, 2016, Genome Biology, 17:206, p. 1-11 (Year: 2016).*
Merialdi et al., Nutritional Interventions during Pregnancy for the Prevention or Treatment of Impaired Fetal Growth: An Overview of Randomized Clinical Trials, 2003, Nutritional Interventions During Pregnancy, p. 1626S-1631S (Year: 2003).*
Chavan-Gautam, Gestation-Dependent Changes in Human Placental Global DNA Methylation Levels, Feb. 8, 2011, Mol. Reprod. Dev., 78:150, p. 1 (Year: 2011).*
Lee et al., Analyzing the cancer methylome through target bisulfite sequencing, 2013, Cancer Letters, 340, p. 171-178 (Year: 2013).*
Wong et al., Noninvasive fetal genomic, methylomic, and transcriptomic analyses using maternal plasma and clinical implication, 2015, Trends in Molecular Medicine, 21(2), p. 98-108 (Year: 2015).*
Gautam et al., Gestation-Dependent Changes in Human Placental Global DNA, 2011, Mol. Reprod. Dev., 78:150, p. 1 (Year: 2011).*
International Search Report and Written Opinion from PCT/CN2017/106663, dated Jan. 22, 2018, 9 pages.
Fan, et al., "Noninvasive Diagnosis of Fetal Aneuploidy by Shotgun Sequencing DNA from Maternal Blood," PNAS 2008, 105:42, 16266-16271.
Extended European Search Report dated Apr. 23, 2020 in EP Patent Application No. 17861749.4. 10 pages.
Lun, Fiona M.F. et al.; "Noninvasive Prenatal Methylomic Analysis by Genomewide Bisulfite Sequencing of Maternal Plasma DNA"; Clinical Chemistry; 2013; vol. 59, Issue 11; pp. 1583-1594.
Jiang, Peiyong et al.; "Gestational Age Assessment by Methylation and Size Profiling of Maternal Plasma DNA: A Feasibility Study"; Clinical Chemistry (Letters to the Editor); Feb. 2017; Epub Dec. 15, 2016 (DOI: 10.1373/clinchem.2016.265702); vol. 63, Issue 2; pp. 606-608.
Hudecova, Irena et al.; "Maternal Plasma Fetal DNA Fractions in Pregnancies with Low and High Risks for Fetal Chromosomal Aneuploidies"; PLoS One; 2014; vol. 9, Issue 2; DOI: 10.1371/journal.pone.0088484; e88484 (7 pages).
Pettker, Christian M., et al. (Committee on Obstetric Practice, the American Institute of Ultrasound in Medicine, and the Society for Maternal-Fetal Medicine); "Committee Opinion No. 700: Methods for Estimating the Due Date"; The American College of Obstetricians and Gynecologists; Obstetrics and Gynecology; May 2017; 129(5); e150-e154; doi: 10.1097/AOG.0000000000002046; 5 pages.

(Continued)

*Primary Examiner* — Olivia M. Wise
*Assistant Examiner* — Kaitlyn L Minchella
(74) *Attorney, Agent, or Firm* — Kilpatrick Townsend & Stockton LLP

(57) ABSTRACT

Temporal variations in one or more characteristics measured from a cell-free DNA sample are used to estimate a gestational age of a fetus. Example characteristics include the methylation level measured from the cell-free DNA sample, size of DNA fragments measured from the cell-free DNA sample (e.g., proportion of fetal-derived DNA fragments longer than a specified size), and ending patterns of the DNA fragments align to a reference genome.

20 Claims, 14 Drawing Sheets
(8 of 14 Drawing Sheet(s) Filed in Color)

(56) References Cited

OTHER PUBLICATIONS

Written Opinion dated Jul. 1, 2020 in SG Patent Application No. 11201903346Q. 13 pages.
Communication pursuant to Article 94(3) EPC dated Dec. 1, 2020 in EP Patent Application No. 17861749.4. 6 pages.
Written Opinion dated Jan. 12, 2021 in SG Patent Application No. 11201903346Q. 10 pages.
Summons to attend oral proceedings pursuant Rule 115(1) EPC dated Dec. 16, 2021 in EP Patent Application No. 17861749.4. 7 pages.
Simpkin, Andrew J. et al.; "Longitudinal analysis of DNA methylation associated with birth weight and gestational age"; Human Molecular Genetics; 2015; vol. 24, No. 13; pp. 3752-3763.

* cited by examiner

GESTATIONAL AGE ASSESSMENT BY METHYLATION AND SIZE PROFILING OF MATERNAL PLASMA DNA

CROSS-REFERENCE TO RELATED APPLICATIONS

This application claims the benefit of U.S. Provisional Patent Application No. 62/410,108, filed on Oct. 19, 2016, the content of which is incorporated herein by reference in its entirety for all purposes.

BACKGROUND

The discovery of cell-free fetal deoxyribonucleic acid (DNA) in maternal plasma has opened up new possibilities for noninvasive prenatal diagnosis (Y M D Lo et al. *Lancet* 1997; 350:485-487). This technology has been rapidly translated into clinical applications, with the detection of fetal-derived, paternally-inherited genes or sequences, e.g., for fetal sex determination and for fetal Rhesus D (RHD) status determination, and, in particular, for screening fetal chromosomal aneuploidies (R W K Chiu et al. 2008 Proc Natl Acad Sci USA; 105:20458-2046). The biological properties of the fetal-derived cell-free DNA in the plasma of a pregnant woman have been demonstrated to exhibit a number of differences from the maternal-derived DNA. For example, the cell-free fetal DNA is generally shorter than the maternal DNA molecules (Y M D Lo et al. 2010 Sci Transl Med; 2: 61ra91) and the overall methylation level of the cell-free fetal DNA in the plasma of a pregnant woman is generally lower than the overall methylation level of maternal-derived DNA (F M F Lun et al. Clin. Chem. 2013; 59:1583-94).

BRIEF SUMMARY

Various embodiments are directed to applications (e.g., diagnostic and treatment applications) of the analysis of a cell-free DNA sample including fetal and maternal DNA (e.g., plasma DNA) from a female pregnant with at least one fetus. Embodiments of one application can use the temporal changes in one or more characteristics measured from a cell-free DNA sample to estimate a gestational age of the at least one fetus. Example characteristics include the methylation level measured from the cell-free DNA sample, the size of DNA fragments measured from the cell-free DNA sample (e.g., proportion of fetal-derived DNA fragments longer than a specified size), and patterns for where ends of DNA fragments align to a reference genome.

In further embodiments, the estimated gestational age may be compared with a gestational age determined using another technique for the biological sample, such as the gestational age determined based on medical history or based on ultrasonic diagnosis. An alarm message can be generated when the estimated gestational age does not match the gestational age determined using other techniques. A corrective action may be taken if the mismatch is caused by administrative errors. Further diagnosis and treatment may be conducted if the mismatch may be caused by pathological reasons, such as pregnancy-associated disorders, such as preeclampsia, preterm labor, intrauterine growth restriction (IUGR), or fetal chromosomal aneuploidies.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A is a plot for the first trimester maternal plasma. FIG. 6B is a plot for the third trimester maternal plasma.

TERMS

Figure 1:
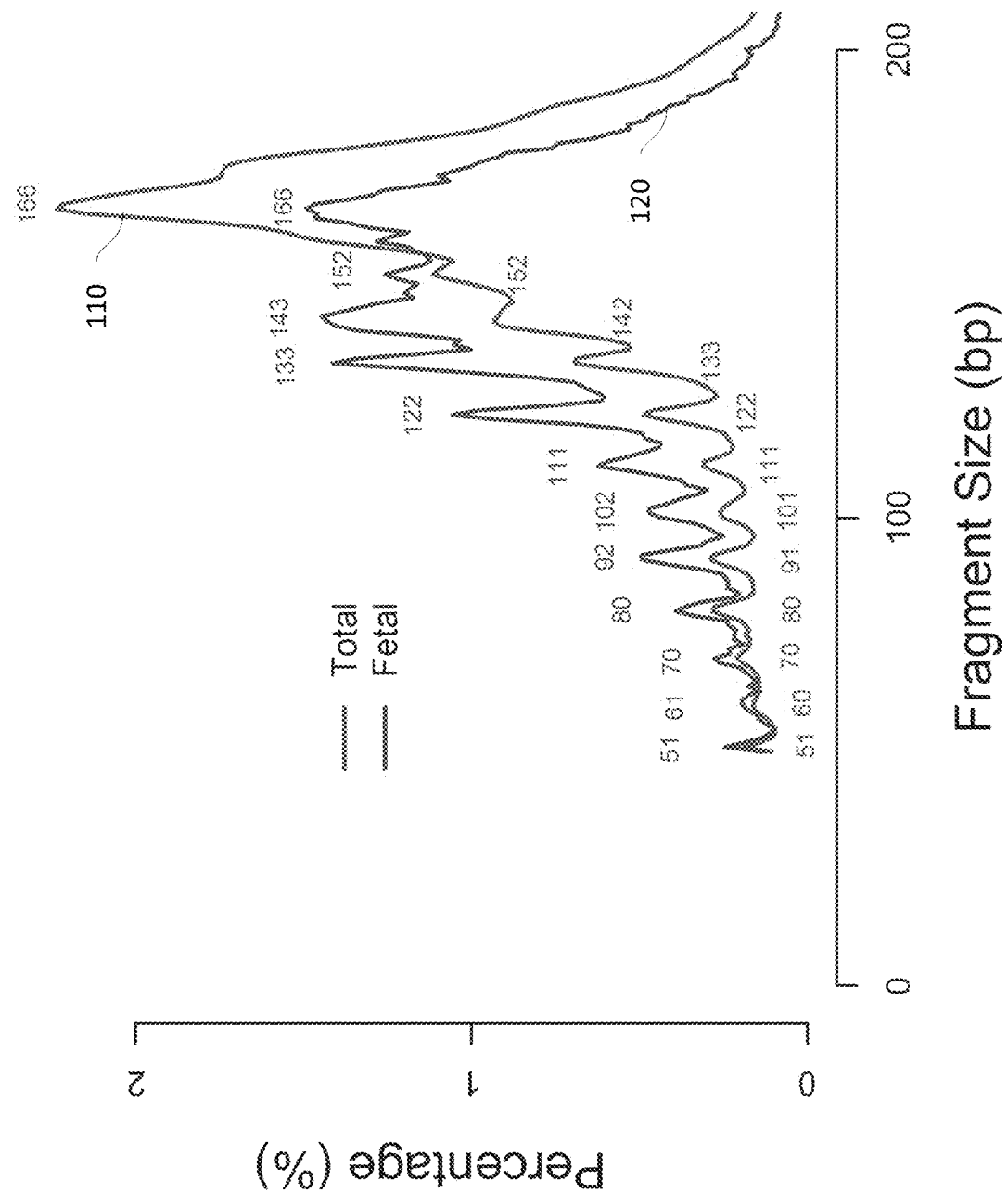
FIG. 1 a plot of a size distribution of circulating cell-free DNA in maternal plasma, according to certain embodiments of the present invention.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissues from different organisms (mother vs. fetus) or to healthy cells vs. tumor cells.

A "biological sample" refers to any sample that is taken from a subject (e.g., a human, such as a pregnant woman, a person with cancer, or a person suspected of having cancer, an organ transplant recipient or a subject suspected of having a disease process involving an organ (e.g., the heart in myocardial infarction, or the brain in stroke, or the hematopoietic system in anemia)) and contains one or more nucleic acid molecule(s) of interest. The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at, for example, 30,000 g for another 10 minutes to remove residual cells.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, copy number variants, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, mRNA, small noncoding RNA, micro RNA (miRNA), Piwi-interacting RNA, and short hairpin RNA (shRNA) encoded by a gene or locus.

The term "gene" refers to a segment of DNA involved in producing a polypeptide chain or transcribed RNA product. It may include regions preceding and following the coding region (leader and trailer) as well as intervening sequences (introns) between individual coding segments (exons).

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "parameter" as used herein refers to a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

As used herein, the term "locus" or its plural form "loci" refers to a location or address of any length of nucleotides (or base pairs) which has a variation across genomes. A "sequence read" refers to a string of nucleotides sequenced from any part or all of a nucleic acid molecule. For example, a sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of organisms typically include multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. As used herein, the term "polymorphism" refers to any inter-individual variation in the human genome, regardless of its frequency. Examples of such variations include, but are not limited to, single nucleotide polymorphism, simple tandem repeat polymorphisms, insertion-deletion polymorphisms, mutations (which may be disease causing) and copy number variations. The term "haplotype" as used herein refers to a combination of alleles at multiple loci that are transmitted together on the same chromosome or chromosomal region. A haplotype may refer to as few as one pair of loci or to a chromosomal region, or to an entire chromosome.

The term "fractional fetal DNA concentration" is used interchangeably with the terms "fetal DNA proportion" and "fetal DNA fraction," and refers to the proportion of fetal DNA molecules that are present in a biological sample (e.g., maternal plasma or serum sample) that is derived from the fetus (Y M D Lo et al. *Am J Hum Genet* 1998; 62:768-775; Lun F M F et al. *Clin Chem* 2008; 54:1664-1672).

The term "size profile" generally relates to the sizes of DNA fragments in a biological sample. A size profile may be a histogram that provides a distribution of the amount of DNA fragments at a variety of sizes. Various statistical parameters (also referred to as size parameters or just parameters) can be used to distinguish one size profile from another. One parameter is the percentage of DNA fragments of a particular size or a range of sizes relative to all DNA fragments or relative to DNA fragments of another size or range.

An "ending position," "end position," "ending pattern," or "ending site" (or just "end") can refer to the genomic coordinate, genomic identity, or nucleotide identity of the outermost base, i.e. at the extremities, of a cell-free DNA molecule, such as a plasma DNA molecule. The end position can correspond to either end of a DNA molecule. Both a start and an end of a DNA molecule can correspond to an ending position. In practice, one end position is the genomic coordinate or the nucleotide identity of the outermost base on one extremity of a cell-free DNA molecule that is detected or determined by an analytical method, such as but not limited to massively parallel sequencing or next-generation sequencing, single molecule sequencing, double- or single-stranded DNA sequencing library preparation protocols, polymerase chain reaction (PCR), or microarray. Such in vitro techniques may alter the true in vivo physical end(s) of the cell-free DNA molecules. Thus, each detectable end may represent the biologically true end or the end is one or more nucleotides inwards or one or more nucleotides extended from the original end of the molecule, such as 5' blunting and 3' filling of overhangs of non-blunt-ended double stranded DNA molecules by the Klenow fragment. The genomic identity or genomic coordinates of the end position could be derived from results of alignment of sequence reads to a human reference genome, such as hg19. The genomic identity or genomic coordinates of the end position could also be derived from a catalog of indices or codes that represent the original coordinates of the human genome. The genomic identity or genomic coordinates of the end position could refer to a position or nucleotide identity on a cell-free DNA molecule that is read by, for example but not limited to, target-specific probes, mini-sequencing, DNA amplification.

A "preferred end" (or "recurrent ending position") refers to an end that is more highly represented or prevalent (e.g., as measured by a rate) in a biological sample having a physiological (e.g., pregnancy) or pathological (disease) state (e.g., cancer) than a biological sample not having such a state or than a biological sample at different time points or stages of the same pathological or physiological state, e.g., before or after treatment. A preferred end therefore has an increased likelihood or probability for being detected in the relevant physiological or pathological state relative to other states. The increased probability can be compared between the pathological state and a non-pathological state, for example, in patients with and without a cancer and quantified as likelihood ratio or relative probability. The likelihood ratio can be determined based on the probability of detecting at least a threshold number of preferred ends in the tested sample or based on the probability of detecting the preferred ends in patients with such a condition than patients without such a condition. Examples for the thresholds of likelihood ratios include, but not limited to: 1.1, 1.2, 1.3, 1.4, 1.5, 1.6, 1.8, 2.0, 2.5, 3.0, 3.5, 4.0, 4.5, 5, 6, 8, 10, 20, 40, 60, 80 and 100. Such likelihood ratios can be measured by comparing relative abundance values of samples with and without the relevant state. Because the probability of detecting a preferred end in a relevant physiological or disease state is higher, such preferred ending positions would be seen in more than one individual with that same physiological or disease state. With the increased probability, more than one cell-free DNA molecule can be detected as ending on a same preferred ending position, even when the number of cell-free DNA molecules analyzed is far less than the size of the genome. Thus, the preferred or recurrent ending positions are also referred to as the "frequent ending positions." In some embodiments, a quantitative threshold may be used to require that the ends be detected at least multiple times (e.g., 3, 4, 5, 6, 7, 8, 9, 10, 15, 20, or 50) within the same sample or same sample aliquot to be considered as a preferred end. A relevant physiological state may include a state when a person is healthy, disease-free, or free from a disease of interest. Similarly, a "preferred ending window" corresponds to a contiguous set of preferred ending positions.

A "rate" of DNA molecules ending on a position relates to how frequently a DNA molecule ends on the position. The rate may be based on a number of DNA molecules that end on the position normalized against a number of DNA molecules analyzed. Accordingly, the rate corresponds to a frequency of how many DNA molecules end on a position, and does not relate to a periodicity of positions having a local maximum in the number of DNA molecules ending on the position.

A "calibration sample" can correspond to a biological sample whose tissue-specific DNA fraction is known or determined via a calibration method, e.g., using an allele specific to the tissue. As another example, a calibration sample can correspond to a sample from which preferred ending positions can be determined. A calibration sample can be used for both purposes. In some cases, the gestational age of a calibration sample may be known.

A "calibration data point" includes a "calibration value" and a measured or known proportional distribution of the DNA of interest (i.e., DNA of a particular tissue type). The calibration value can be a relative abundance as determined for a calibration sample, for which the proportional distribution of the tissue type is known. The calibration data points may be defined in a variety of ways, e.g., as discrete points or as a calibration function (also called a calibration curve or calibration surface). The calibration function could be derived from additional mathematical transformation of the calibration data points.

The term "sequencing depth" refers to the number of times a locus is covered by a sequence read aligned to the locus. The locus could be as small as a nucleotide, or as large as a chromosome arm, or as large as the entire genome. Sequencing depth can be expressed as 50×, 100×, etc., where "X" refers to the number of times a locus is covered with a sequence read. Sequencing depth can also be applied to multiple loci, or the whole genome, in which case x can refer to the mean number of times the loci or the haploid genome, or the whole genome, respectively, is sequenced. Ultra-deep sequencing can refer to at least 100×in sequencing depth.

A "separation value" corresponds to a difference or a ratio involving two values. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, such as a difference or ratio of the natural logarithms (ln) of the two values. A separation value can include a difference and a ratio.

A "relative abundance" is a type of separation value that relates an amount (one value) of cell-free DNA molecules ending within one window of genomic position to an amount (another value) of cell-free DNA molecules ending within another window of genomic positions. The two windows may overlap, but would be of different sizes. In other implementations, the two windows would not overlap. Further, the windows may be of a width of one nucleotide, and therefore be equivalent to one genomic position.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1).

The terms "cutoff" and "threshold" refer to predetermined numbers used in an operation. For example, a cutoff size can refer to a size above which fragments are excluded. A threshold value may be a value above or below which a particular classification applies. Either of these terms can be used in either of these contexts.

A "local maximum" can refer to a genomic position (e.g., a nucleotide) at which the largest value of the parameter of interest is obtained when compared with the neighboring positions or refer to the value of the parameter of interest at such a genomic position. As examples, the neighboring positions can range from 50 bp to 2000 bp. Examples for the parameter of interest include, but are not limited to, the number of fragments ending on a genomic position, the number of fragments overlapping with the position, or the proportion of fragments covering the genomic position that are larger than a threshold size. Many local maxima can occur when the parameter of interest has a periodic structure. A global maximum is a specific one of the local maxima. Similarly, a "local minimum" can refer to a genomic position at which the smallest value of the parameter of interest is obtained when compared with the neighboring positions or refer to the value of the parameter of interest at such a genomic position.

"DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example, CHG and CHH, where H is adenine, cytosine, or thymine. Cytosine methylation may also be in the form of 5-hydroxymethylcytosine. Non-cytosine methylation, such as N6-methyladenine, has also been reported.

A "methylome" provides a measure of an amount of DNA methylation at a plurality of sites or loci in a genome. The methylome may correspond to all of the genome, a substantial part of the genome, or relatively small portion(s) of the genome. A "fetal methylome" corresponds to the methylome of a fetus of a pregnant female. The fetal methylome can be determined using a variety of fetal tissues or sources of fetal DNA, including placental tissues and cell-free fetal DNA in maternal plasma. A "tumor methylome" corresponds to the methylome of a tumor of an organism (e.g., a human). The tumor methylome can be determined using tumor tissue or cell-free tumor DNA in maternal plasma. The fetal methylome and the tumor methylome are examples of a methylome of interest. Other examples of methylomes of interest are the methylomes of organs (e.g., methylomes of brain cells, bones, the lungs, the heart, the muscles and the kidneys, etc.) that can contribute DNA into a bodily fluid (e.g., plasma, serum, sweat, saliva, urine, genital secretions, stools fluid, diarrheal fluid, cerebrospinal fluid, secretions of the gastrointestinal tract, pancreatic secretions, intestinal secretions, sputum, tears, aspiration fluids from breast and thyroid, etc.). The organs may be transplanted organs.

A "plasma methylome" is the methylome determined from the plasma or serum of an animal (e.g., a human). The plasma methylome is an example of a cell-free methylome since plasma and serum include cell-free DNA. The plasma methylome is also an example of a mixed methylome since it is a mixture of fetal/maternal methylome or tumor/patient methylome. The "placental methylome" can be determined from a chorionic villus sample (CVS) or a placental tissue sample (e.g., obtained following delivery). The "cellular methylome" corresponds to the methylome determined from cells (e.g., blood cells) of the patient. The methylome of the blood cells is called the blood cell methylome (or blood methylome).

A "site" corresponds to a single site, which may be a single base position or a group of correlated base positions, e.g., a CpG site. A "locus" may correspond to a region that includes multiple sites. A locus can include just one site, which would make the locus equivalent to a site in that context.

The "methylation index" for each genomic site (e.g., a CpG site) refers to the proportion of sequence reads showing methylation at the site over the total number of reads covering that site. The "methylation density" of a region is the number of reads at sites within the region showing methylation divided by the total number of reads covering the sites in the region. The sites may have specific characteristics, e.g., being CpG sites. Thus, the "CpG methylation density" of a region is the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g., 50-kb or 1-Mb, etc. A region could be the entire genome or a chromosome or part of a chromosome (e.g., a chromosomal arm). The methylation index of a CpG site is the same as the methylation density for a region when the region only includes that CpG site. The "proportion of methylated cytosines" refers the number of cytosine sites, "C's", that are shown to be methylated (for example unconverted after bisulfite conversion) over the total number of analyzed cytosine residues, i.e. including cytosines outside of the CpG context, in the region. The methylation index, methylation density and proportion of methylated cytosines are examples of "methylation levels."

A "methylation profile" (also called methylation status) includes information related to DNA methylation for a region in a genome. Information related to DNA methylation can include, but not limited to, a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome.

DETAILED DESCRIPTION

Temporal variations of a fragmentation pattern, a size, and methylation level of DNA fragments in a maternal cell-free DNA (e.g., maternal plasma DNA) and the applications are described, for example, to determine a gestational age of a fetus. Various embodiments are directed to applications (e.g., diagnostic and treatment applications) of the analysis of a cell-free DNA sample including fetal and maternal DNA (e.g., plasma DNA) from a female pregnant with at least one fetus. Various applications can use a property of the maternal plasma DNA to determine the gestational age of a fetus. For example, temporal changes in one or more characteristics measured from a cell-free DNA sample can be used to estimate a gestational age of the at least one fetus. In some embodiments, a proportion of fetal-derived long (or short) DNA fragments, the methylation level of the cell-free (fetal) DNA, or a combination thereof may be used to determine the gestational age of a fetus. In some embodiments, the ending patterns of DNA fragments in maternal plasma may be used to determine the gestational age of a fetus.

The estimated gestational age may be compared with a gestational age determined using another technique for the biological sample, such as the gestational age determined based on medical history or based on ultrasonic diagnosis. An alarm message can be generated when the estimated gestational age does not match the gestational age determined using other techniques. A corrective action may be taken if the mismatch is caused by administrative errors. Further diagnosis and treatment may be conducted if the mismatch may be caused by pathological reasons, such as pregnancy-associated disorders, such as preeclampsia, pre-term labor, intrauterine growth restriction (IUGR), fetal chromosomal aneuploidies, etc.

I. Fragmentation of Cell-Free DNA

Cell-free DNA fragmentation refers to the process whereby high molecular weight (or long) DNA molecules (such as DNA molecules in the nucleus of a cell) are cleaved, broken, or digested to short fragments when cell-free DNA molecules are generated or released. Cell-free DNA occurs naturally in the form of short fragments. A non-random fragmentation process of cell-free DNA may take place, to a certain extent, in various types of biological samples that contain cell-free DNA, such as plasma, serum, urine, saliva, cerebrospinal fluid, pleural fluid, amniotic fluid, peritoneal fluid, and ascitic fluid.

It has been shown that cell-free DNA, such as plasma DNA, is generally shorter and less intact, namely of poor intact probability, or poorer integrity, within open chromatin domains, including around transcription start sites, and at locations between nucleosomal cores, such as at the linker positions (Strayer et al. Prenat Diagn 2016, 36:614-621).

Because each different tissue has its characteristic gene expression profile which may be regulated by factors including chromatin structure and nucleosomal positioning, cell-free DNA patterns of intact probability or integrity at certain genomic locations of, for example, plasma DNA, may be used as signatures or hallmarks of the tissue origin of those DNA molecules. For example, a fetal-specific allele can be identified by analyzing a maternal plasma sample from a pregnant woman and comparing detected alleles to alleles detected in a maternal-only sample. A fetal-specific single nucleotide polymorphism (SNP) allele would be useful for identifying fetal-specific cell-free DNA.

Plasma DNA mostly consists of short fragments of less than 200 base pairs (bp) (Lo et al. Sci Transl Med 2010; 2(61):61ra91). The fragmentation pattern of plasma DNA is non-random (Snyder et al. Cell 2016; 164: 57-68 and WO 2016/015058 A2). A peak may be observed at 166 bp in the size distribution of plasma DNA. The plasma DNA fragmentation pattern may be influenced by many factors, such as nucleosomal positioning, transcription factor binding sites, DNase cutting or hypersensitive sites, expression profiles (Snyder et al. Cell 2016; 164: 57-68 and PCT WO 2016/015058; Ivanov et al. BMC Genomics 2015; 16 Suppl 13:S1), and DNA methylation profiles (Lun et al. Clin Chem 2013; 59: 1583-1594) in the genome of the cells that have contributed the plasma DNA molecules. Plasma DNA fragmentation pattern may be used for various applications.

II. Sizes of Plasma DNA Fragments

Not all cell-free DNA molecules are of the same length. Some molecules are shorter than others. It is known that cell-free fetal DNA molecules in maternal plasma are generally shorter than the maternally-derived ones (Chan K C A et al. Clin Chem 2004; 50:88-92; Lo Y M D et al. Sci Transl Med 2010; 2:61ra91). Thus, the presence of fetal DNA may result in a shift in the overall size distribution of maternal plasma DNA. The degree of shifting may be associated with the fractional concentration of fetal DNA. Therefore, the fractional fetal DNA concentration in maternal plasma may be determined by measuring particular values of the size profile of maternal plasma DNA. Some example techniques for determining sizes of plasma DNA fragments and performing a size-based analysis for a prenatal diagnosis of a sequence imbalance in a biological sample obtained from a pregnant female subject may be found in, for example, WO 2011054936 A1, entitled "Size-based Genomic Analysis" and WO 2013/132305 A1, entitled "Size-based Analysis of Fetal DNA Fraction in Maternal Plasma," the contents of which are incorporated herein by reference in their entireties for all purposes.

A. Determining Sizes of Plasma DNA Fragments

The size distribution of plasma DNA can be determined, for example, but not limited to, using real-time PCR, targeted enrichment, electrophoresis, and mass spectrometry analysis. In various embodiments, the size of a DNA fragment can be represented by a length, a molecular mass, or a measured parameter that is proportional to the length or mass, such as the mobility in a electrophoretogram and the time required for the DNA fragment to travel a fixed distance in electrophoresis or mass spectrometer. In another example, one can stain the DNA with an intercalating fluorescence dye, such as ethidium bromide or SYBR Green, where the amount of dye bound to the DNA fragment will be proportional to the length of the DNA fragment. One can determine the amount of dye bound to the DNA fragment by the intensity of the emitted fluorescence when UV light is shone on the sample.

One method with which the sizes of a number of DNA molecules can be measured is massively parallel genomic sequencing. This can be performed by, for example, the Illumina Genome Analyzer platform (using sequencing by synthesis) (Bentley D R et al. Nature 2008; 456: 53-59), the ABI SOLiD (using sequencing by ligation) (McKernan et al. Genome Res 2009; 19: 1527-1541), the Roche 454 platform (Marguelis et al. Nature 2005; 437:376-380), and the Helicos single molecule sequencing platform (Harris et al. Science 2008; 320: 106-109). Other massively parallel sequencing platforms can also be used, such as the Pacific Biosciences (single molecule, real-time (SMRT™) technology) (Eid et al. Science 2009; 323: 133-138), nanopore sequencing (Clarke J et al. Nat Nanotechnol 2009; 4: 465-470), semiconductor sequencing (e.g., by Ion Torrent (iontorrent.com), etc.

One example technique to obtain the size information of DNA fragments from such genomic sequencing is to perform paired-end (PE) sequencing, in which both ends of a DNA molecule (fragment) are sequenced. Then, the sequences corresponding to both ends of the molecule can be mapped back to a reference genome (e.g., a reference human genome or a reference horse genome, or the genome of any animal of interest). Sequencing libraries of maternal plasma DNA may be constructed as previously described (Lo Y M et al. *Sci Transl Med* 2010; 2:61ra91), except that a 6-base barcode may be introduced to the DNA molecules of each plasma sample through a triple-primer PCR amplification. In one embodiment, both ends are each sequenced at a length that is long enough to be mapped back, individually for each end, to the reference human genome (e.g., about 10-24 bases or 25-36 bases). In another embodiment, only a proportion of sequences can be mapped back without mismatch to the non-repeat region of the human genome. In one aspect, the mapping may be unambiguous if both sequences together are used in the mapping. In this scenario, even though each of the ends might be too short to be mapped back with confidence, using both sequences can provide unambiguous mapping. The size of the molecule can be worked out by, for example, subtraction of the genomic coordinates of the ends of the two sequences. In other embodiments, alignment may not be unique and mismatches may be allowed.

In another embodiment, the size of the molecule can be obtained by a complete, or close to complete, sequencing of the whole DNA molecule, instead of just the two ends. This can be done efficiently by sequencing platforms with relatively long read-lengths, such as the Roche 454 platform, the Pacific Biosciences single molecule, real-time (SMRT™) technology, and the Ion Torrent technology (iontorrent.com).

In another embodiment, the size of the molecule can be obtained by a complete, or close to complete, sequencing of the whole DNA molecule, instead of just the two ends. This can be done efficiently by sequencing platforms with relatively long read-lengths, such as the Roche 454 platform, the Pacific Biosciences single molecule, real-time (SMRT™) technology, and the Ion Torrent technology (www.iontorrent.com).

The throughput of the above-mentioned sequencing-based methods can be increased with the use of indexing or barcoding (Cronn et al. Nucleic Acids Res 2008; 36: e122). Thus, a sample (or patient)-specific index (or barcode) can be added to nucleic acid fragments in a particular nucleic acid sequencing library. Then, a number of such libraries, each with a sample (or patient)-specific index (or barcode), are mixed together and sequenced together. Following the sequencing reactions, the sequencing data can be harvested from each sample or patient based on the barcode or the index. This strategy can increase the throughput and thus the cost-effectiveness of the current invention.

In another embodiment, the nucleic acid molecules in the biological sample can be selected or fractionated prior to size analysis. In one variant, the nucleic acid molecules are treated with a device (e.g., a microarray or a solution containing probes) which would preferentially bind nucleic acid molecules from selected loci in the genome (e.g., one of chromosomes 21, 18, 13, or X), then the size analysis can be performed on the bound subset of the nucleic acid molecules. In such an embodiment, a Nimblegen sequence capture system (nimblegen.com/products/seqcap/index.html) or an Agilent SureSelect Target Enrichment System (opengenomics.com/SureSelect_Target_Enrichment_System), or similar platforms can be used. In another embodiment, the unbound nucleic acid subset can be differentially removed or degraded or digested.

In some embodiments, the paired-end (PE) reads meeting the following criteria can be used for subsequent analysis: (1) the individual members of each suggested pair are both sequenced on the same cluster position on the sequencing flow cell and be aligned to the same chromosome with the correct orientation as expected for the human reference genome; (2) the sequenced reads of both members of the pair could be aligned to the repeat-masked human reference genome without any nucleotide mismatch; (3) the sequenced reads of each member of the pair have a uniqueness score >4; and (4) the pairs demonstrate an insert size less than 600 bp. The size of each aligned sequence is then calculated according to the position of each of the two ends.

In addition to using massively parallel sequencing, the analysis of the size distribution of plasma DNA can be achieved by a electrophoresis process. The electrophoresis process measures a time for a fragment to move through a medium. Particles of different sizes take different times to move through the medium. The time duration a DNA fragment takes to reach the sensor is positively correlated with the size of the DNA fragment. An analyzer, such as Agilent 2100 Bioanalyzer, can automatically convert the time duration to fragment size by comparing the running time of the test sample to those of a mixture of DNA fragments with known lengths (i.e., a DNA ladder). Thus, in one embodiment, microfluidic electrophoresis of sequencing library of maternal plasma DNA can be performed to determine the size distribution of the maternal plasma DNA.

In some embodiments, the plasma DNA can be amplified by a whole genome amplification system known to those skilled in the art, such as the Rubicon Genomics PlasmaPlex WGA kit (rubicongenomics.com/products). The amplified products can then be analyzed by the analyzer. In yet other embodiments, the amplified products can be analyzed by an electrophoretic system from, for example, Caliper (caliperls.com/products/labchip-systems). In yet other embodiments, the size distribution of plasma DNA can be analyzed directly, without amplification, using for example, a nanopore-based sequencer (e.g., from Oxford Nanopore Technologies (nanoporetech.com)), or a Helico DNA sequencer (helicosbio.com).

At least some embodiments can work with any single molecule analysis platform in which the chromosomal origin and the length of the molecule can be analyzed using, for example, electrophoresis, optical methods (e.g., optical mapping and its variants, en.wikipedia.org/wiki/Optical_mapping#cite_note-Nanocoding-3, and Jo et al. Proc Natl Acad Sci USA 2007; 104: 2673-2678), fluorescence-based method, probe-based methods, digital PCR (microfluidics-based, or emulsion-based, such as BEAMing (Dressman et al. Proc Natl Acad Sci USA 2003; 100: 8817-8822) or RainDance (raindancetech.com/technology/per-genomics-research.asp)), rolling circle amplification, mass spectrometry, melting analysis (or melting curve analysis), molecular sieving, etc. As an example for mass spectrometry, a longer molecule would have a larger mass (an example of a size value).

B. Size Distribution

The following examples show that one can measure the size profile, for example, by paired-end massively parallel sequencing or by electrophoresis (e.g., using a Bioanalyzer). The latter example is particularly useful because electrophoresis using a Bioanalyzer is a quick and relatively cheap procedure. This would allow one to rapidly perform this analysis as a quality control measure before one would subject a plasma DNA sample to the relatively expensive sequencing process.

FIG. 1 shows a plot 100 of a size distribution of circulating cell-free DNA in maternal plasma according to certain embodiments of the present invention. A size distribution can be obtained by measuring a size of DNA fragments and then counting the number of DNA fragments at various sizes, e.g., within the range of 50 base pairs (bp) to about 220 bp. Plot 100 shows two distributions. Distribution 110 is for all DNA fragments in the maternal plasma sample, and distribution 120 is only for DNA that is from the fetus. The horizontal axis is the size of the DNA fragments in base pairs (bp). The vertical axis is the percentage of measured DNA fragments with various sizes.

In FIG. 1, distribution 120 of fetal-derived DNA in maternal plasma shows that the average size of fetal-derived DNA is shorter than that of the maternally derived ones (Chan K C et al. *ClinChem* 2004; 50:88-92.) There is a reduction in the fraction of DNA fragments with 166 bp, and an increase in the proportion of shorter DNA fragments with less than 150 bp for the fetal-derived DNA (Lo Y M et al. Sci Transl Med 2010 2:61ra91).

Figure 2A:
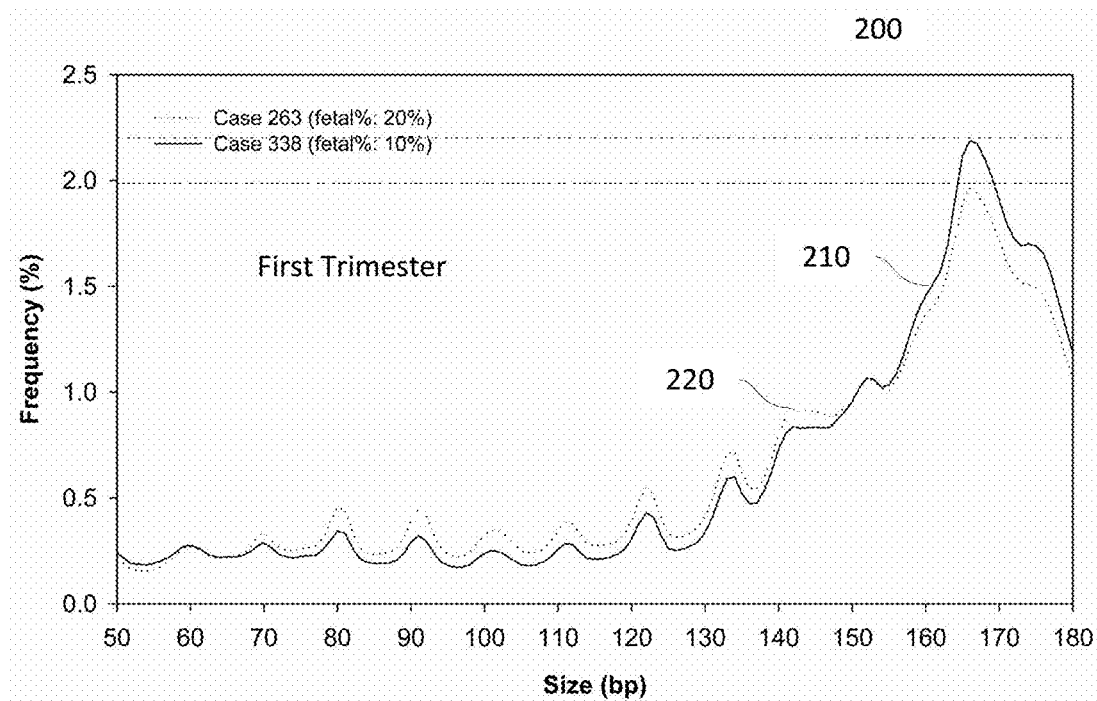
FIG. 2A shows a plot of size distributions of DNA fragments in two maternal plasma samples ($1^{st}$ trimester pregnancies) with different fractional fetal DNA concentrations, according to certain embodiments of the present invention.

FIG. 2A shows a plot 200 of size distributions of DNA fragments in two maternal plasma samples ($1^{st}$ trimester pregnancies) with different fractional fetal DNA concentrations, according to certain embodiments of the present invention. Both of these two pregnant women are carrying male fetuses. The fractional fetal DNA concentrations are determined from the proportion of sequences from the Y chromosome among the total sequenced DNA fragments. Both samples are taken from pregnant women during the first trimester of their pregnancies. Case 338 (solid line 210) with a fractional fetal DNA concentration 10% has a lower fractional fetal DNA concentration than Case 263 (dotted line 220) with a fractional fetal DNA concentration 20%. When compared with Case 263, Case 338 has a higher peak at 166 bp, but the peaks for size below 150 bp are lower. In other words, DNA fragments shorter than 150 bp are more abundant in Case 263, whereas DNA fragments of approximately 166 bp are more abundant in Case 338. These observations are consistent with the hypothesis that the relative amounts of short and long DNA may be correlated to the fractional fetal DNA concentration.

Figure 2B:
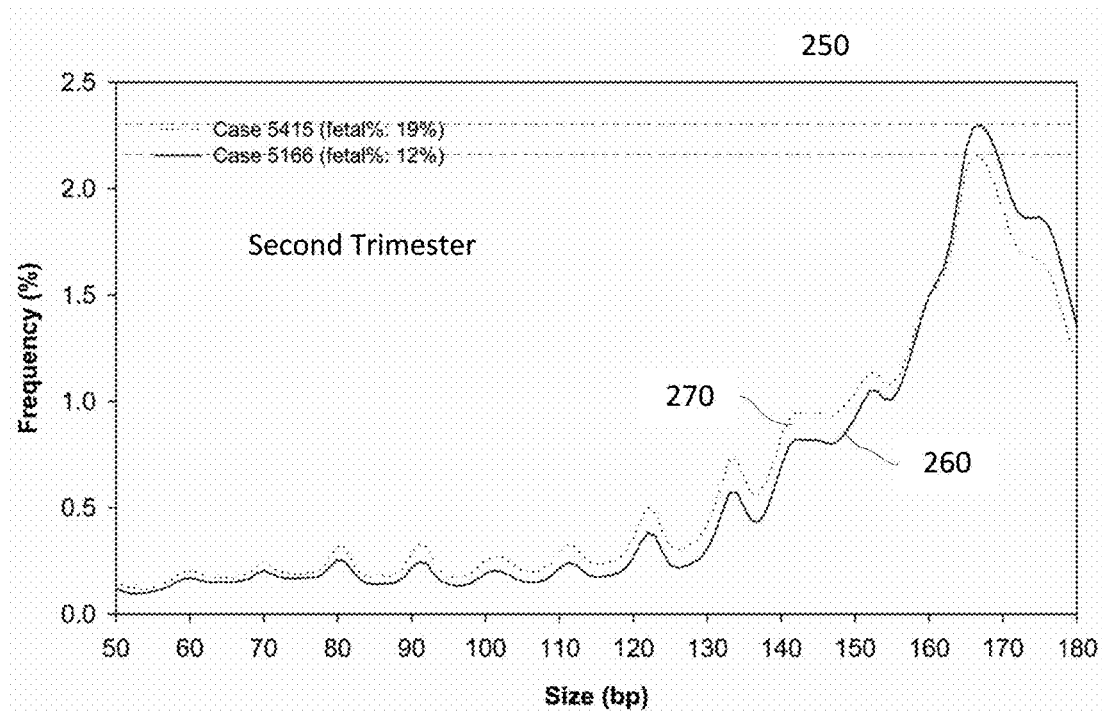
FIG. 2B shows a plot of size distributions of DNA fragments in two maternal plasma samples ($2^{nd}$ trimester pregnancies) with different fractional fetal DNA concentrations, according to certain embodiments of the present invention.

FIG. 2B shows a plot 250 of size distributions of DNA fragments in two maternal plasma samples ($2^{nd}$ trimester pregnancies) with different fractional fetal DNA concentrations, according to certain embodiments of the present invention. Both samples are taken from pregnant women during the second trimester. Both of these two pregnant women are carrying male fetuses. The fractional fetal DNA concentrations are determined from the proportion of sequences from the Y chromosome among the total sequenced DNA fragments. Similar to the previous example shown in FIG. 2A, case 5415 (dotted line 270) with a higher fractional fetal DNA concentration of about 19% has higher peaks for sizes below 150 bp whereas case 5166 (solid line 260) with a lower fractional fetal DNA concentration 12% has a higher peak at 166 bp.

FIGS. 2A and 2B also show that the proportion of long DNA fragments is higher in the second trimester than that in the first trimester.

C. Proportion of Short/Long DNA Fragments in Maternal Plasma DNA

Various parameters can provide a statistical measure of a size profile of DNA fragments in the biological sample. A parameter can be defined using the sizes of all of the DNA fragments analyzed, or just a portion. In one embodiment, a parameter indicates a relative abundance of short and long DNA fragments, where the short and long DNA fragments may correspond to specific sizes or ranges of sizes.

To investigate if the overall size distribution of maternal plasma DNA can be used for determining the gestational age of a fetus, different parameters may be used to quantify the relative abundance of short and long DNA fragments, and determine the correlation between these parameters and gestational ages. For example, one such parameter is the proportion of DNA fragments of 150 bp or below, which may be labeled as CF (size ≤150), where CF refers to cumulative frequency. Thus, CF (size ≤150) refers to the cumulative frequency of fragments with a size less than or equal to 150 bp.

Figure 3:
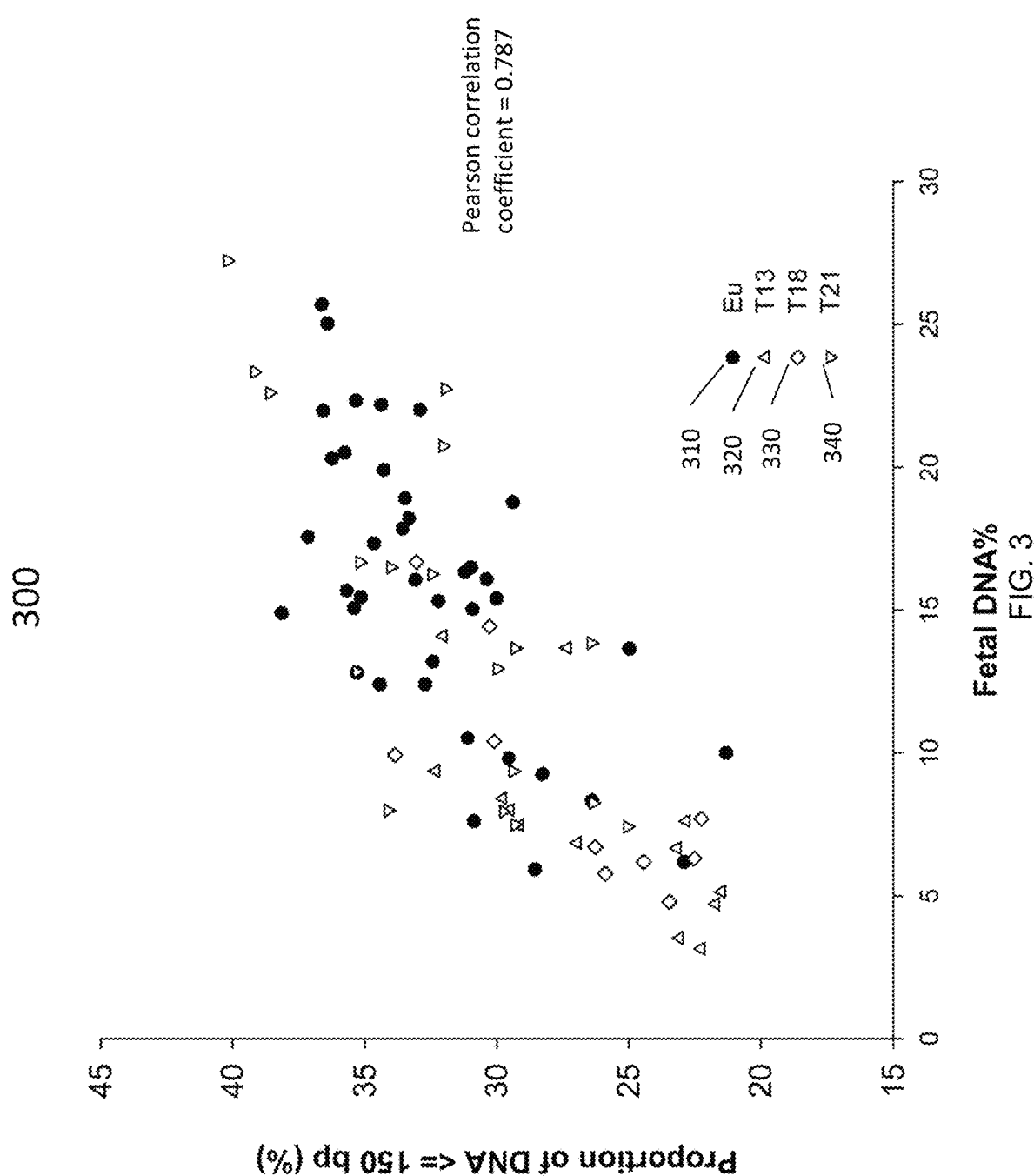
FIG. 3 is a plot showing a proportion of DNA fragments that have 150 or less base pairs for samples having various fetal DNA percentage in maternal plasma, according to certain embodiments of the present invention.

FIG. 3 is an example plot 300 showing a proportion of DNA fragments that have 150 or less base pairs for samples having various fetal DNA percentages in maternal plasma, according to certain embodiments of the present invention. The proportion of DNA, for example, ≤150 bp, is plotted against the fractional fetal DNA concentration for 80 maternal plasma samples. The euploid samples are represented by filled circles 310. The trisomy 13 (T13) samples are represented by unfilled triangles 320. The trisomy 18 (T18) samples are represented by unfilled rhombus 330, and the trisomy 21 (T21) samples are represented by inverted unfilled triangles 340.

FIG. 3 shows that there is a positive correlation between the fractional fetal DNA concentration and the proportion of DNA fragments with 150 or less base pairs for all samples (Pearson correlation coefficient=0.787). The positive correlation between the size parameter and the fractional fetal DNA concentration appears to be consistent across samples with different fetal chromosomal status. These results suggest that the analysis of the size parameter may be useful for estimating the fractional fetal DNA concentration in a maternal plasma sample, or vice versa.

As indicated by FIGS. 2A and 2B and discussed in detail below with respect to FIG. 7, experimental data has suggested that the proportion of fetal-derived long DNA fragments also increases as the gestational age progresses. Thus, it is also possible to use the proportion of fetal-derived long DNA fragments to determine the gestational age of a fetus.

III. Methylation of Maternal Plasma

DNA methylation is one of the frequently studied epigenetic mechanisms. Methylation of DNA mostly occurs in the context of the addition of a methyl group to the 5' carbon of cytosine residues among CpG dinucleotides. Cytosine methylation adds a layer of control to gene transcription and DNA function. For example, hypermethylation of gene promoters enriched with CpG dinucleotides (termed CpG islands) is typically associated with repression of gene function.

The human placenta exhibits a plethora of peculiar physiological features involving DNA methylation. On a global level, placental tissues are hypomethylated when compared with most somatic tissues. At the gene level, the methylation status of selected genomic loci is a specific signature of placental tissues. Both the global and locus-specific methylation profiles show gestational-age dependent changes.

Studies of the DNA methylation profile of placental tissues have provided insights into the pathophysiology of pregnancy-associated or developmentally related diseases, such as preeclampsia and intrauterine growth restriction. Imprinted genes, namely genes for which expression is dependent on the parental origin of alleles, serve key functions in the placenta. Disorders in genomic imprinting are associated with developmental disorders, such as Prader-Willi syndrome and Angelman syndrome. Altered profiles of genomic imprinting and global DNA methylation in placental and fetal tissues have been observed in pregnancies resulted from assisted reproductive techniques (H Hiura et al. 2012 Hum Reprod; 27: 2541-2548). A number of environmental factors (e.g., maternal smoking) (K E Haworth et al. 2013 Epigenomics; 5: 37-49), maternal dietary factors (X Jiang et al. 2012 FASEB J; 26: 3563-3574), and maternal metabolic status (e.g., diabetes) (N Hajj et al., Diabetes. doi: 10.2337/db12-0289) have been associated with epigenetic aberrations of the offspring. Examples of determination and use of methylation profiles of various tissues and samples can be found in, for example, WO2014/043763 A1, entitled "Non-Invasive Determination of Methylome of Fetus or Tumor from Plasma," the content of which is incorporated herein by reference in its entirety for all purposes.

A. Techniques for Methylation Profiling

Various techniques may be used to investigate the placental methylome. For example, sodium bisulfite, a chemical that modifies unmethylated cytosine residues to uracil and leaves methylated cytosine unchanged, converts the differences in cytosine methylation into a genetic sequence difference for further interrogation. Thus, a method of studying cytosine methylation may include treating tissue DNA with sodium bisulfite followed by direct sequencing of individual clones of bisulfite-converted DNA molecules. After the analysis of multiple clones of DNA molecules, the cytosine methylation pattern and quantitative profile per CpG site can be obtained.

Methylation-sensitive restriction enzymes that typically digest unmethylated DNA may provide a low cost approach to study DNA methylation. Data generated from such studies may be limited to loci with the enzyme recognition motifs, and the results may not be quantitative. Immunoprecipitation of DNA bound by anti-methylated cytosine antibodies can be used to survey large segments of the genome, but tends to bias towards loci with dense methylation due to the higher strength of antibody binding to such regions. Microarray-based approaches based on a priori design of the interrogation probes and hybridization efficiencies between the probes and the target DNA may also be used.

To interrogate a methylome comprehensively, some embodiments use massively parallel sequencing (MPS) to provide genome-wide information and quantitative assessment of the level of methylation on a per nucleotide and per allele basis. It is feasible to perform bisulfite conversion followed by genome-wide MPS (R Lister et al. 2008 Cell; 133: 523-536).

Certain embodiments may enable interrogation of a fetal methylome comprehensively, noninvasively, and serially. In one embodiment, genome-wide bisulfite sequencing is used to analyze cell-free fetal DNA molecules that are found in the circulation of pregnant women. Despite the low abundance and fragmented nature of plasma DNA molecules, it is possible to assemble a high resolution fetal methylome from maternal plasma and serially observe the changes with pregnancy progression. Given the intense interest in noninvasive prenatal testing (NIPT), embodiments can provide a powerful new tool for fetal biomarker discovery or serve as a direct platform for achieving NIPT of fetal or pregnancy-associated diseases. The fetal methylome can be derived from data from the genome-wide bisulfite sequencing of various samples. This technology can be applied for methylation profiling in pregnancies complicated with preeclampsia, intrauterine growth retardation, or preterm labor. For such complicated pregnancies, this technology can be used serially because of its noninvasive nature, to allow for the monitoring, prognostication, and/or response to treatment.

During bisulfite modification, unmethylated cytosines are converted to uracils and subsequently to thymines after PCR amplifications, while the methylated cytosines would remain intact (M Frommer et al. 1992 Proc Natl Acad Sci USA; 89:1827-31). After sequencing and alignment, the methylation status of an individual CpG site could thus be inferred from the count of methylated sequence reads "M" (methylated) and the count of unmethylated sequence reads "U" (unmethylated) at the cytosine residue in CpG context. Using the bisulfite sequencing data, the entire methylomes of maternal blood, placenta, and maternal plasma can be constructed. The mean methylated CpG density (also called methylation density MD) of specific loci in the maternal plasma can be calculated using the following equation:

$$MD = \frac{M}{M+U},$$

where M is the count of methylated reads and U is the count of unmethylated reads at the CpG sites within the genetic locus. If there is more than one CpG site within a locus, then M and U correspond to the counts across the sites.

Methylation profiling can be performed using massively parallel sequencing (MPS) of bisulfite converted plasma DNA. The MPS of the bisulfite converted plasma DNA can be performed in a random or shotgun fashion. The depth of the sequencing can be varied according to the size of the region of interest. In another embodiment, the region(s) of interest in the bisulfite converted plasma DNA can first be captured using a solution-phase or solid-phase hybridization-based process, followed by the MPS.

The massively parallel sequencing can be performed using a sequencing-by-synthesis platform such as the Illumina, a sequencing-by-ligation platform such as the SOLiD platform from Life Technologies, a semiconductor-based sequencing system such as the Ion Torrent or Ion Proton platforms from Life Technologies, or single molecule sequencing system such as the Helicos system, the Pacific Biosciences system, or a nanopore-based sequencing system. Nanopore-based sequencing includes using nanopores that are constructed using, for example, lipid bilayers and protein nanopore, and solid-state nanopores (such as those that are graphene based). Because single-molecule-sequencing platforms could allow the methylation status of DNA molecules (including N6-methyladenine, 5-methylcytosine, and 5-hydroxymethylcytosine) to be elucidated directly without bisulfite conversion (B A Flusberg et al. 2010 Nat Methods; 7: 461-465; J Shim et al. 2013 Sci Rep; 3:1389. doi: 10.1038/srep01389), the use of such platforms could allow the methylation status of non-bisulfite converted sample DNA (e.g., plasma DNA) to be analyzed.

Besides sequencing, other techniques can be used. In one embodiment, methylation profiling can be performed by methylation-specific PCR, methylation-sensitive restriction enzyme digestion followed by PCR or ligase chain reaction followed by PCR. In some embodiments, the PCR is a form of single-molecule or digital PCR (B Vogelstein et al. 1999 Proc Natl Acad Sci USA; 96: 9236-9241). In some embodiments, the PCR can be a real-time PCR. In some embodiments, the PCR can be multiplex PCR.

B. Methylation of Plasma DNA Molecules

DNA molecules are present in human plasma at low concentrations and in a fragmented form, typically in lengths resembling mononucleosomal units (Y M D Lo et al. 2010 Sci Transl Med; 2: 61ra91; and Y W Zheng at al. 2012 Clin Chem; 58: 549-558). Despite these limitations, a genome-wide bisulfite-sequencing pipeline is able to analyze the methylation of plasma DNA molecules. In yet other embodiments, a single-molecule sequencing platform would allow the methylation status of DNA molecules to be elucidated directly without bisulfite conversion (B A Flusberg et al. 2010 Nat Methods; 7: 461-465; J Shim et al. 2013 Sci Rep; 3:1389. doi: 10.1038/srep01389), and thus would allow non-bisulfite converted plasma DNA to be used to determine the methylation levels of plasma DNA or to determine the plasma methylome. Such platforms can detect N6-methyladenine, 5-methylcytosine, and 5-hydroxymethylcytosine, which can provide improved results (e.g., improved sensitivity or specificity) related to the different biological functions of the different forms of methylation. Such improved results can be useful when applying embodiments for the detection or monitoring of specific disorders, such as preeclampsia or a particular type of cancer.

Bisulfite sequencing can also discriminate between different forms of methylation. In one embodiment, one can include additional steps that can distinguish 5-methylcytosine from 5-hydroxymethylcytosine. One such approach is oxidative bisulfite sequencing (oxBS-seq), which can elucidate the location of 5-methylcytosine and 5-hydroxymethylcytosine at single-base resolution (M J Booth et al. 2012 Science; 336: 934-937; M J Booth et al. 2013 Nature Protocols; 8: 1841-1851). In oxBS-seq, specific oxidation of 5-hydroxymethylcytosine to 5-formylcytosine by treatment with potassium perruthenate (KRuO4), followed by the conversion of the newly formed 5-formylcytosine to uracil using bisulfite conversion would allow 5-hydroxymethylcytosine to be distinguished from 5-methylcytosine. Hence, a readout of 5-methylcytosine can be obtained from a single oxBS-seq run, and 5-hydroxymethylcytosine levels are deduced by comparison with the bisulfite sequencing results. In another embodiment, 5-methylcytosine can be distinguished from 5-hydroxymethylcytosine using Tet-assisted bisulfite sequencing (TAB-seq) (M Yu et al. 2012 Nat Protoc; 7: 2159-2170). TAB-seq can identify 5-hydroxymethylcytosine at single-base resolution, as well as determine its abundance at each modification site. This method involves β-glucosyltransferase-mediated protection of 5-hydroxymethylcytosine (glucosylation) and recombinant mouse Tet1(mTet1)-mediated oxidation of 5-methylcytosine to 5-carboxylcytosine. After the subsequent bisulfite treatment and PCR amplification, both cytosine and 5-carboxylcytosine (derived from 5-methylcytosine) are converted to thymine (T), whereas 5-hydroxymethylcytosine will be read as C.

C. Methylation Levels across Methylomes

The methylation of maternal plasma DNA, maternal blood cells, and placental tissue may be studied to determine methylation levels. The methylation levels may be determined for repeat regions, non-repeat regions, and overall.

Figure 4A:
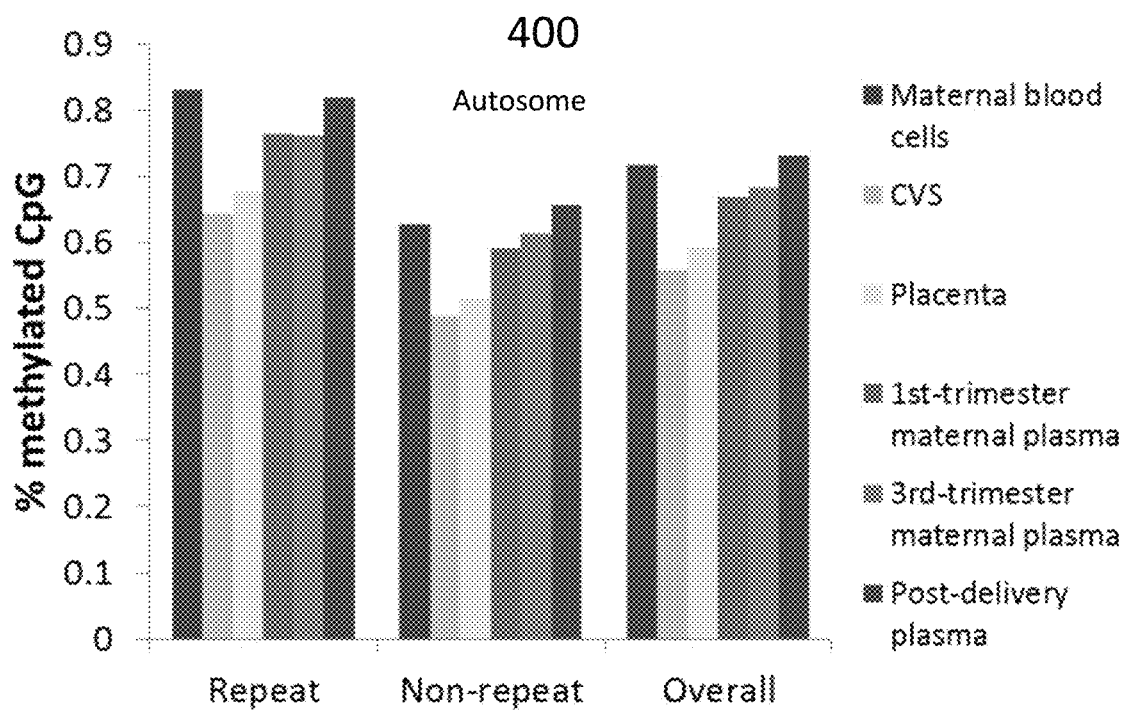
FIG. 4A shows a bar chart of percentage of methylated CpG sites in Autosomes among samples collected during pregnancy, according to certain embodiments of the present invention.
Figure 4B:
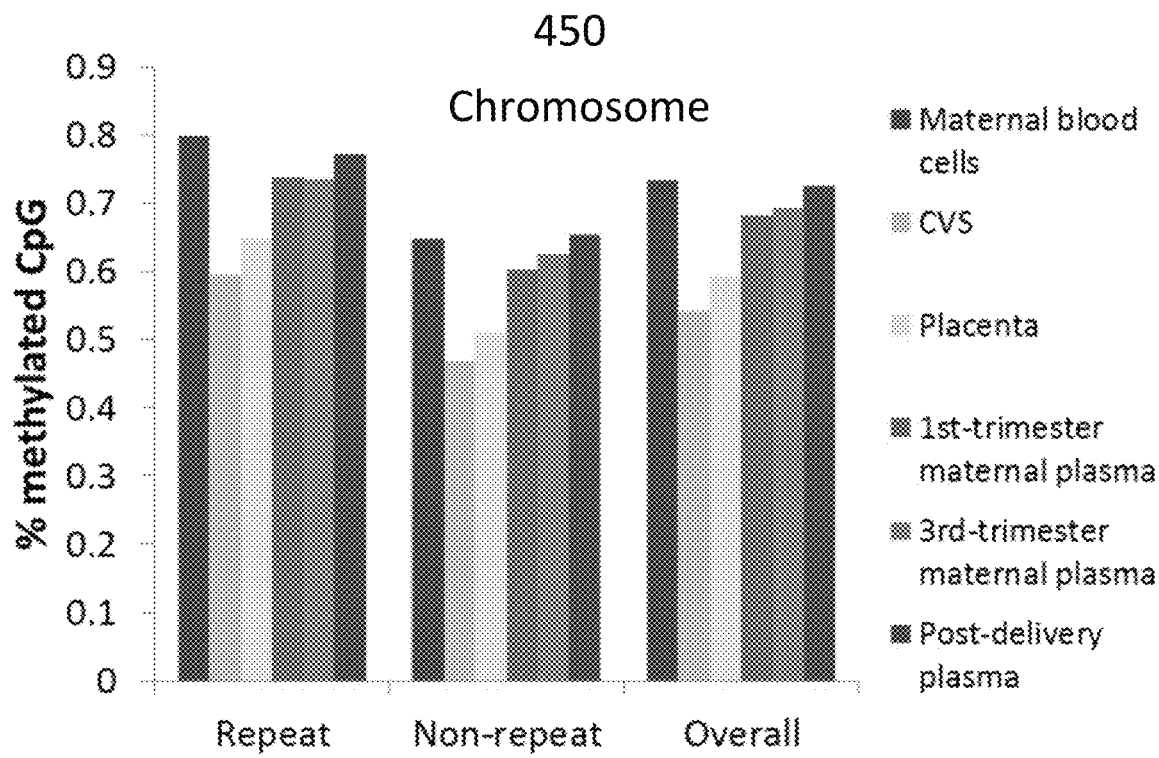
FIG. 4B shows a bar chart of percentage of methylated CpG sites in Chromosome X among samples collected during pregnancy, according to certain embodiments of the present invention.

FIG. 4A shows a bar chart 400 of percentage of methylated CpG sites in Autosomes among samples collected during pregnancy, according to certain embodiments of the present invention. FIG. 4B shows a bar chart 450 of percentage of methylated CpG sites in Chromosome X among samples collected from the pregnancy, according to certain embodiments of the present invention. The overall proportions of methylated CpGs are 66.93% and 68.22% for the first and third trimester maternal plasma samples, respectively. The proportion results obtained from non-pregnant individuals are lower than that of the first trimester maternal blood cell sample but higher than that of the chorionic villus sample (CVS) and term placental tissue samples. The percentage of methylated CpGs for the post-delivery maternal plasma sample is 73.1%, which is similar to the blood cell data. These trends are observed in CpGs distributed over all autosomes as well as chromosome X and spanned across both the non-repeat regions and multiple classes of repeat elements of the human genome.

Both the repeat and non-repeat elements in the placenta are found to be hypomethylated relative to maternal blood cells. The results are concordant to the findings in the literature that the placenta is hypomethylated relative to other tissues, including peripheral blood cells.

Between about 71% to 72% of the sequenced CpG sites are methylated in the blood cell DNA from a pregnant woman, a non-pregnant woman, and an adult male. These data are comparable with the report of 68.4% of CpG sites of blood mononuclear cells being methylated reported by Y Li et al. 2010 PLoS Biol; 8: e1000533. Consistent with the previous reports on the hypomethylated nature of placental tissues, 55% and 59% of the CpG sites are methylated in the CVS and term placental tissue, respectively.

FIGS. 4A and 4B also show differences in methylation levels between maternal plasma at the first trimester and maternal plasma at the third trimester. For example, FIGS. 4A and 4B indicate that the methylation level of the CVS (or first trimester) samples. is lower than the methylation level of the placenta (third trimester) samples. Normalized methylation levels of fetal DNA molecules in the plasma samples also show significant difference between the methylation level of fetal DNA molecules in first trimester plasma samples and the methylation level of fetal DNA molecules in the third trimester plasma samples.

As shown in FIGS. 4A and 4B, the overall methylation level of buffy coat samples is about 71.7%, the overall methylation level of the first trimester plasma samples is about 66.93%, and the overall methylation level of the third trimester plasma samples is about 68.22%. Based on the known fractions of fetal DNA molecules in the first trimester plasma samples (e.g., 14.4%) and the third trimester plasma samples (e.g., 33.9%), the methylation levels of the fetal DNA molecules in the first and third trimester plasma samples may be determined based on:

$$M = M_1 * (1-f) + M_2 * f,$$

where M is the overall methylation level of plasma samples, $M_1$ is the methylation level of buffy coat, $M_2$ is the methylation level of fetal DNA molecules, and f is the fraction of the fetal DNA molecules in the plasma samples. Thus, the methylation level of fetal DNA molecules can be determined by:

$$M_2=(M-M_1*(1-f))/f.$$

Based on the data shown in FIGS. 4A and 4B and the above equation, it can be determined that the methylation level of the fetal DNA molecules is about 38.6% for the first trimester plasma samples and about 61.4% for the third trimester plasma samples.

It is noted that, as described above, in some cases, the methylation level of the fetal DNA molecules in a sample may be determined based on the overall methylation level of the cell-free DNA molecules in the sample and the fraction of the fetal DNA molecules in the sample. In some cases, the methylation level of the fetal DNA molecules in a sample may be determined differently. For example, fetal DNA molecules may be identified from the biological sample based on, for example, fetal-specific allele in the molecules, and the fetal DNA molecules may then be analyzed to determine the methylation level of fetal DNA molecules.

As indicated by FIGS. 4A and 4B and discussed in detail below with respect to FIG. 7, experimental data has also suggested that the methylation level of fetal-derived long DNA fragments also increases as the gestational age progresses. Further, it may be possible to identify methylation markers whose methylation levels would be more strongly correlated with the gestational age. Thus, it is also possible to use the methylation level of fetal-derived long DNA fragments to determine the gestational age of a fetus.

The methylation levels associated with maternal plasma sample, maternal blood cells, and the placental sample may be compared against one another to determine if the sets of methylation levels are different between each other. For example, the methylation levels can be compared using, for example, the Mann-Whitney test. A P-value of, for example, ≤0.01, and can be considered as statistically significantly different, although other values may be used, where a lower number would reduce false positive regions.

IV. Relationship Between Gestational Age and Methylation Level and/or Fragment Size As described above, the sizes of cell-free DNA in maternal plasma are reported to be positively correlated with the DNA methylation level (F M F Lun et al. Clin Chem 2013; 59:1583-94). The relationships between the fragment size and methylation level of maternal plasma DNA at different gestational ages are studied to determine the correlations among gestational ages, methylation levels, and/or size profiles of maternal plasma DNA.

A. Example Relationships between Fragment Size and Methylation Level

Figure 5:
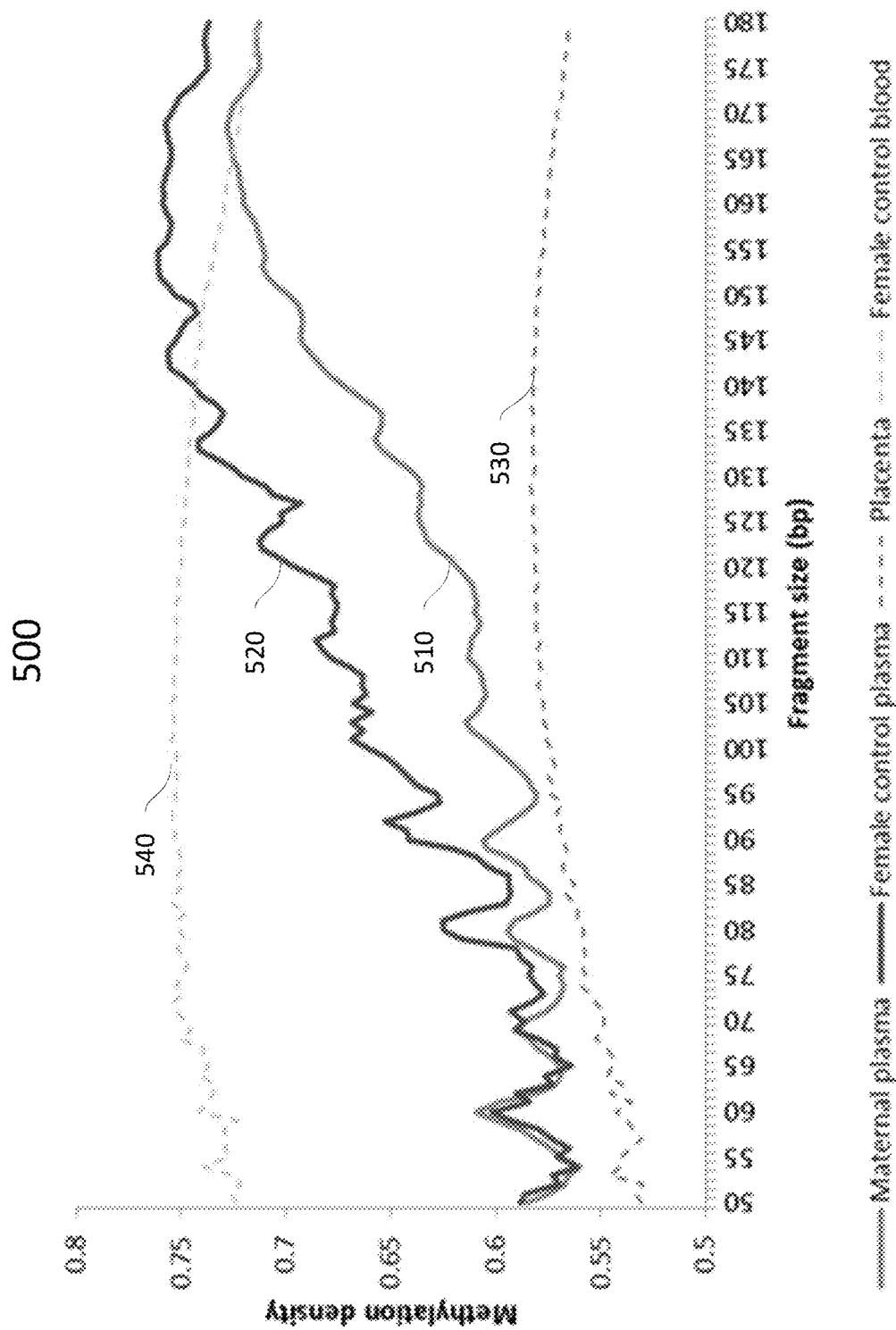
FIG. 5 is a plot of methylation density versus fragment size for maternal plasma, adult female control plasma, placental tissue, and adult female control blood, according to certain embodiments of the present invention.

FIG. 5 is a plot 500 of methylation density versus fragment size for maternal plasma (line 510), adult female control plasma (line 520), placental tissue (line 530) and adult female control blood (line 540), according to certain embodiments of the present invention. For DNA molecules of the same size and containing at least one CpG site, their mean methylation density is calculated. The relationship between the sizes of the DNA molecules and their methylation densities can be plotted. Specifically, the mean methylation density is determined for each fragment length ranging from 50 bp up to 180 bp for sequenced reads covering at least 1 CpG site. Notice that the methylation density increases with the plasma DNA size and peaks at around 166-167 bp. This pattern, however, is not observed in the placenta and control blood DNA samples which are fragmented using an ultrasonicator system.

Figure 6A:
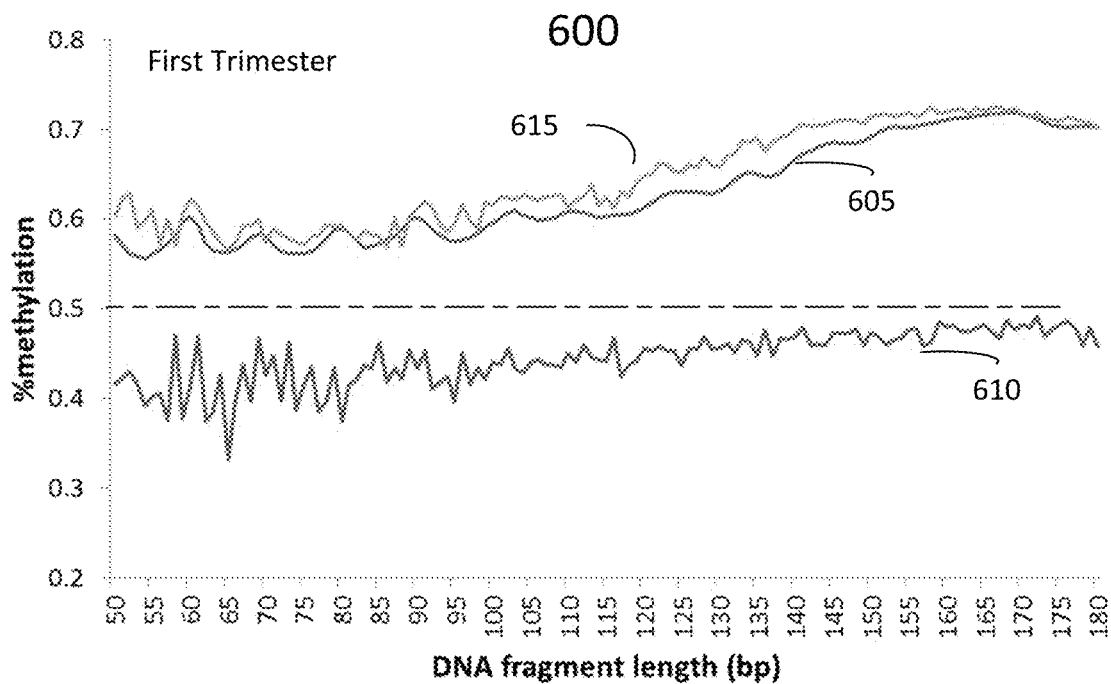
FIGS. 6A and 6B show plots of methylation densities versus size of plasma DNA molecules, according to certain embodiments of the present invention.
Figure 6B:
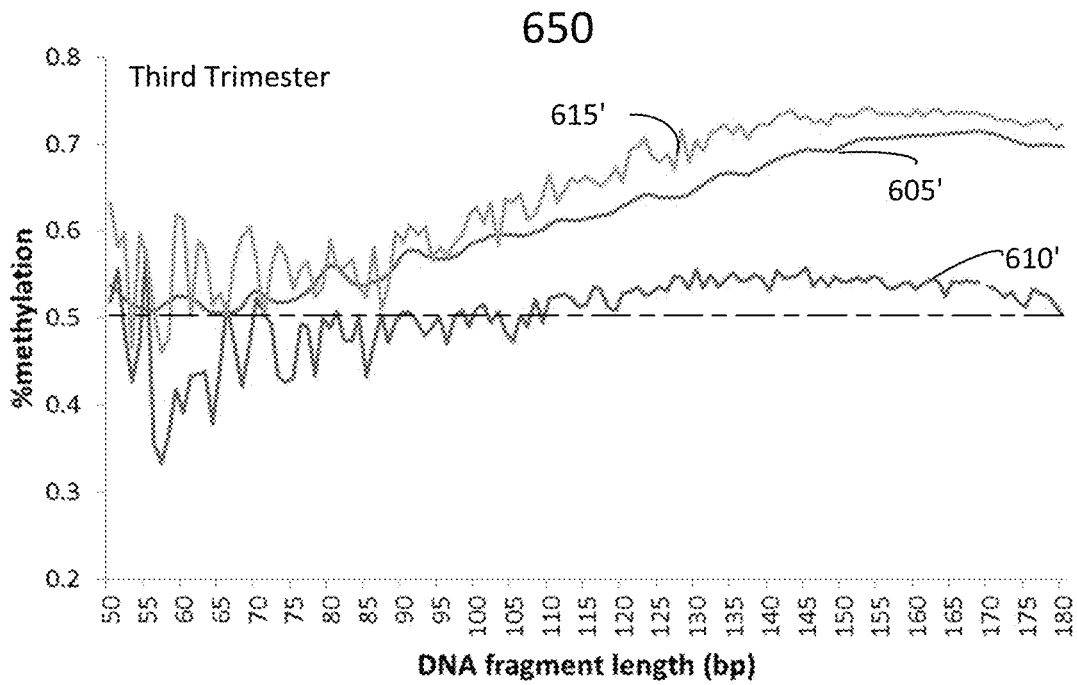

FIGS. 6A and 6B show plots of methylation densities and size of plasma DNA molecules at different gestational ages, according to certain embodiments of the present invention. FIG. 6A is a plot 600 for the first trimester maternal plasma. FIG. 6B is a plot 650 for the third trimester maternal plasma. Data for all the sequence reads that cover at least one CpG site are represented by the blue curves 605 and 605'. Data for reads that also contain a fetal-specific SNP allele is represented by the red curves 610 and 610'. Data for reads that also contain a maternal-specific SNP allele is represented by the green curves 615 and 615'.

Reads that contained a fetal-specific SNP allele are considered to have been derived from fetal DNA molecules. Reads that contained a maternal-specific SNP allele are considered to have been derived from maternal DNA molecules. In general, DNA molecules with high methylation densities are longer in size. This trend is present in both the fetal and maternal DNA molecules in both the first and third trimesters.

B. Relationship of Fragment Size and Methylation level at Different Gestational Ages FIGS. 6A (first trimester) and 6B (third trimester) show the relations between methylation densities and sizes plasma DNA molecules at different gestational ages. The methylation densities and/or the sizes of plasma DNA molecules may also be correlated with gestational ages.

Figure 7:
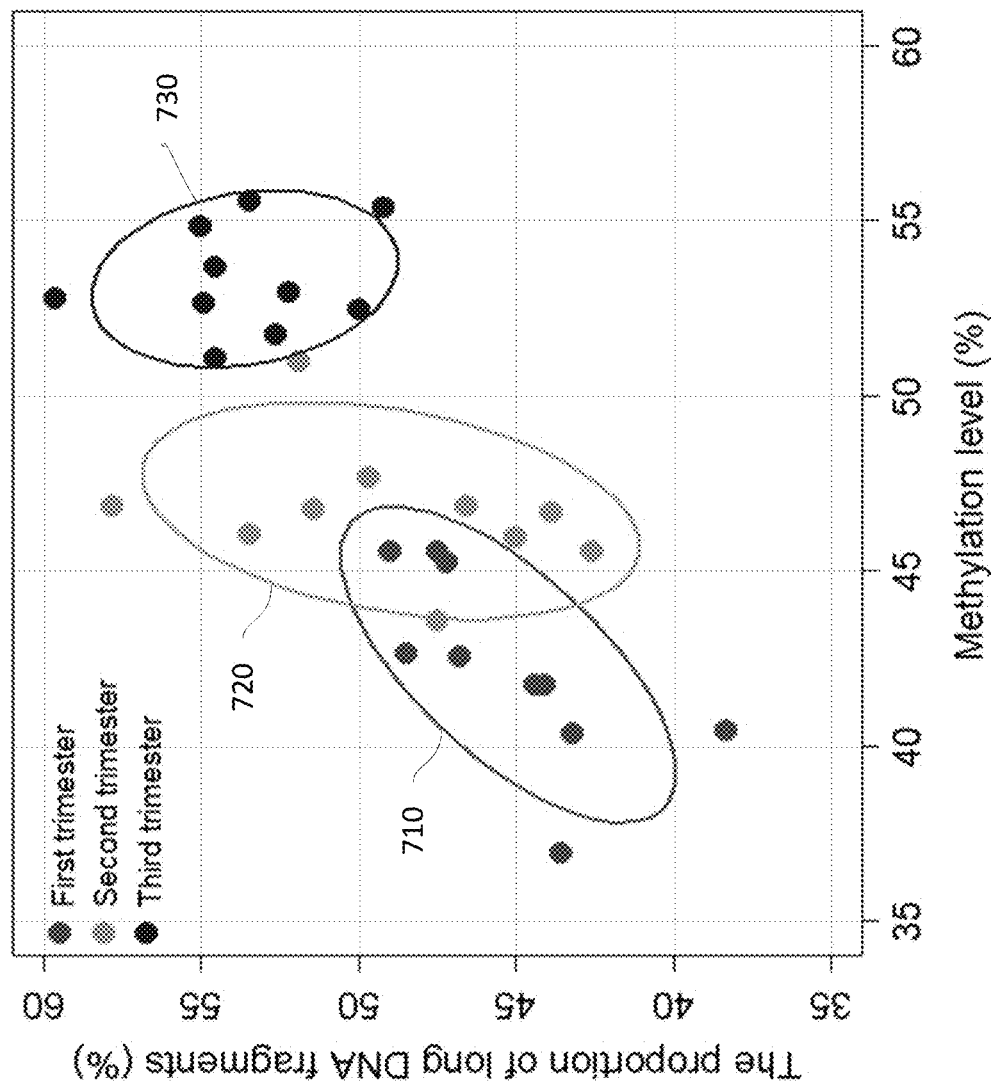
FIG. 7 illustrates correlations among gestational ages, methylation levels, and size profiles of maternal plasma DNA, where the first-, second-, and third-trimester samples are represented in red, green and blue dots, respectively; the horizontal axis represents the methylation level; and the vertical axis represents the proportion of fetal-derived long fragments (e.g., ≥150 bp), according to certain embodiments of the present invention.

FIG. 7 illustrates correlations among gestational ages, methylation levels, and size profiles of maternal plasma DNA based on a study, where the first-, second-, and third-trimester samples are represented in red, green and blue dots, respectively, the horizontal axis represents the methylation level, and the vertical axis represents the proportion of fetal-derived long fragments (e.g., ≥150 bp).

In the study, peripheral blood samples are obtained from 10 pregnant women at each of the first (12-14 weeks), second (20-23 weeks), and third (38-40 weeks) trimesters and the plasma and maternal buffy coat are harvested for each case. Fetal samples are also obtained by chorionic villus sampling, amniocentesis, and sampling of the placenta, respectively, depending on whether the study is for the first, second, or third trimester. The maternal buffy coat and fetal samples are genotyped using a microarray platform (HumanOmni2.5, Illumina). The median of the number of informative SNP loci is 195,331 (with a range of 146,428-202,800), for which the mother is homozygous and the fetus is heterozygous. Plasma DNA molecules that carry fetal-specific alleles are identified as derived from the fetus. The median fetal DNA fraction among those samples was 17.1% (range: 7.0-46.8%). Genomewide paired-end bisulfite sequencing is applied to plasma DNA samples and analyzed by the Methy-Pipe software package as described in, for example, F M F Lun et al. Clin Chem 2013; 59:1583-94 and P. Jiang et al. PLoS One 2014; 9:e100360. About 52-186 million (with a median value of 103 million) mapped and non-duplicated paired-end reads are obtained for each case. The fetal-specific reads cover about 36,115 (within a range of 17,252-57,980), 35,914 (within a range of 22,815-68, 624), and 134,671 (within a range of 92,580-176,996) CpG sites for the first-, second-, and third-trimester maternal plasma samples, respectively. The methylation level of the fetal DNA is expressed as the proportion of CpGs that are methylated among the sequenced fetal-specific plasma DNA molecules of each sample. The median methylation levels are found to be about 42.2% (with a range of 37.0-45.7%), 46.8% (with a range of 43.6-51.0%), and 52.9% (with a range of 51.1-55.6%) for the first-trimester plasma samples (710), second-trimester plasma samples (720), and third-trimester plasma samples (730), respectively. The methylation level of fetal DNA is found to increase as the gestational age progressed, rising up by about 25% (p-value <0.0001, Mann-Whitney test) from the first trimester to the third trimester. The methylation levels in the second-trimester group are between those values for the first- and third-trimester groups. However, there is no statistically significant change (p-value=0.2, Mann-Whitney test) for the methylation levels of maternal-derived DNA from the first trimester (not shown) with a median of 68.9% and a range of 65.7-71.4%) to the third trimesters (not shown) with a median of 70.0% and a range of 69.4-71.3%).

The size profile of maternal plasma DNA is determined via the coordinates of the outermost nucleotide at each end of the aligned paired-end reads as described above. As FIGS. 5, 6A, and 6B, FIG. 7 shows that the sizes of cell-free DNA in maternal plasma are positively correlated with the DNA methylation level. Quantifying the proportion of long DNA fragments for each plasma sample also shows that the proportion of fetal-derived long DNA fragments (≥150 bp) also increases as the gestational age progresses, as shown in FIG. 7 and indicated in FIGS. 2A and 2B. FIG. 7 shows that the median of the proportions of fetal-derived long DNA fragments is about 45.6% (with a range of 38.3-49.9%), 48.6% (with a range of 42.6-57.7%), and 54.0% (with a range of 49.2-59.7%) for the first-, second-, and third-trimester plasma samples, respectively. A median of the proportion of fetal-derived long DNA increased by about 18% (p-value <0.0001, Mann-Whitney test) from the first trimester (about 45.6%) to the third trimester (about 54.0%). On the other hand, the median of the proportions of maternal-derived long DNA (not shown) increased only by about 7% (p-value=0.001, Mann-Whitney test) from the first trimester (with a median of 73.8% and a range of 69.6-75.7%) to the third trimester (with a median of 78% and a range of 73.5-79%). Such long fetal DNA in the third trimester was concentrated in a range of 150 to 200 bp. The proportion of fetal-derived long DNA in the second-trimester group is between the values of the first- and third-trimester groups.

As also shown in FIG. 7, the methylation level, alone or in combination with the proportion of fetal-derived long DNA, may create a reasonable separation between samples from the three gestational age groups. Thus, the molecular gestational age may be determined based on the methylation level alone or in combination with the proportion of fetal-derive long DNA using maternal plasma DNA.

Even though FIG. 7 shows clusters with respect to the first, second, and third trimesters, those skilled in the art would understand that the data may be clustered using different time resolutions, such as by weeks, by bi-weeks, or by months during the pregnancy.

C. Example Method

Figure 8:
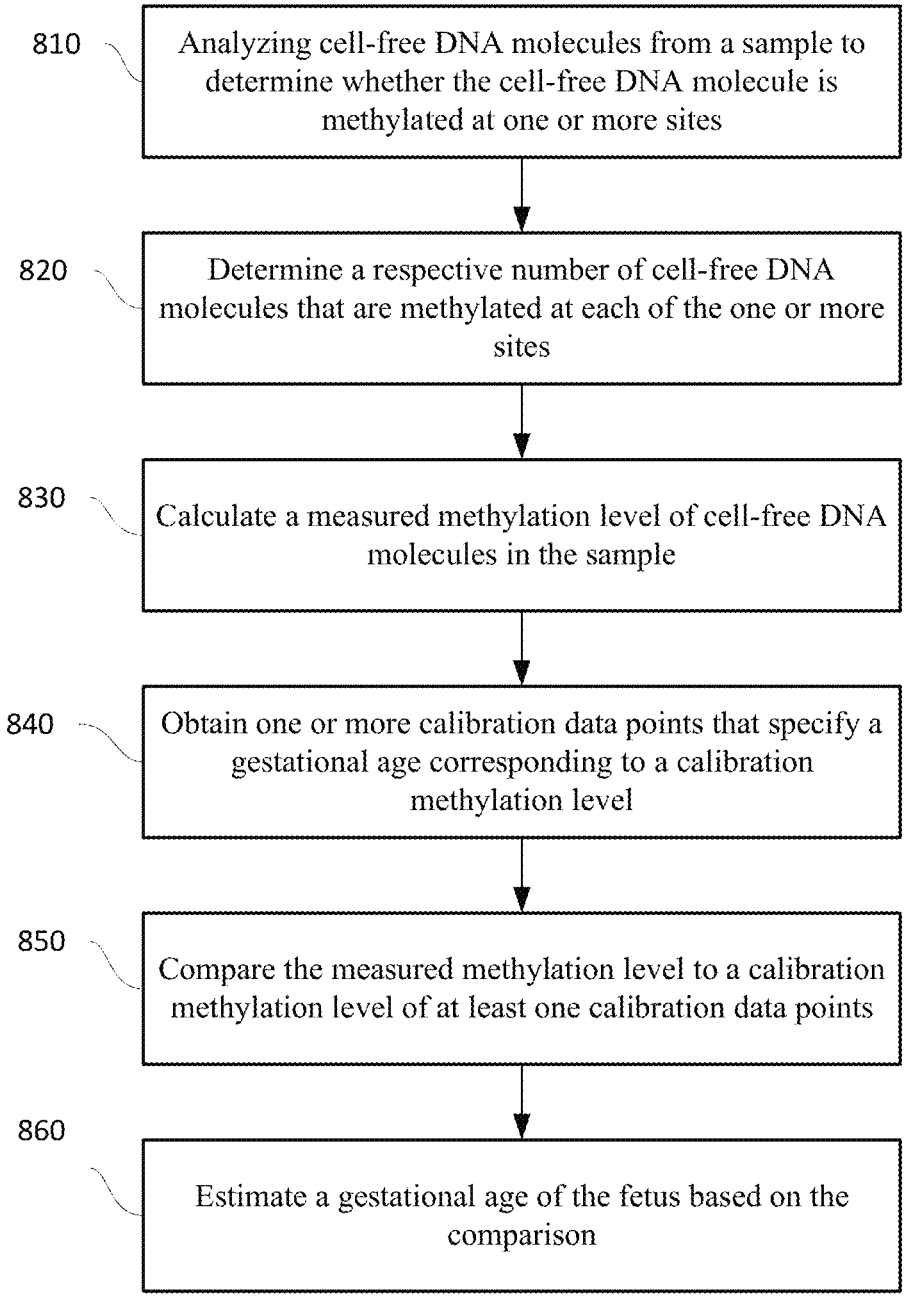
FIG. 8 is a flow chart illustrating an example method of determining gestational age of a fetus based on the methylation level (and/or the proportion of fetal-derived long DNA), according to certain embodiments of the present invention.

FIG. 8 is a flow chart 800 illustrating an example method for determining gestational age of a fetus based on the methylation level (and/or the proportion of fetal-specific long DNA fragments) in a maternal sample including cell-free DNA molecules, according to certain embodiments of the present invention At block 810, a biological sample collected from a pregnant female subject may be analyzed. The biological sample many be a sample with cell-free DNA molecules, such as, a plasma, serum, urine, saliva, cerebrospinal fluid, pleural fluid, amniotic fluid, peritoneal fluid, or ascitic fluid sample. Each cell-free DNA molecule may be analyzed by determining a location of the cell-free DNA molecule in a genome of the fetus or the female subject and determining whether the cell-free DNA molecule is methylated at one or more sites. For example, as described above, massively parallel sequencing (MPS) may be used for methylation profiling. In some embodiments, fetal DNA molecules, rather than all cell-free DNA molecules, may be identified and analyzed. For example, a fetal-specific allele may be identified by analyzing a maternal plasma sample from a pregnant woman and comparing detected alleles to alleles detected in a maternal-only sample, and the fetal-specific allele may be used for identifying fetal-specific cell-free DNA molecules, and determining the proportion of fetal-specific long DNA fragments.

At block 820, for each of the one or more sites, a respective number of cell-free DNA molecules that are methylated at the site may be determined based on the analysis of each cell-free DNA molecule performed in block 810.

At block 830, a measured methylation level of cell-free DNA molecules in the biological sample may be calculated based on the respective numbers of cell-free DNA molecules methylated at the one or more sites determined at block 820. In some embodiments, the methylation level of fetal DNA molecules in a sample may be determined based on the overall methylation level of the cell-free DNA molecules in the sample and the fraction of the fetal DNA molecules in the sample, as described above with respect to FIGS. 4A and 4B. The methylation level of the cell-free DNA molecules in the sample may be determined based on the respective numbers of cell-free DNA molecules methylated at the one or more sites determined at block 820 and the total number of cell-free DNA molecules in the sample. Alternatively, a fetal-specific allele can be identified by analyzing a maternal plasma sample from a pregnant woman and comparing detected alleles to alleles detected in a maternal-only sample, and the fetal-specific allele may be used for identifying fetal-specific cell-free DNA molecules in a maternal plasma sample. The identified fetal-specific cell-free DNA fragments may be profiled using various techniques described above to determine the methylation level of fetal-specific DNA fragments.

At block 840, one or more calibration data points may be obtained, where the one or more calibration data points are determined using a plurality of calibration samples with known gestational ages and including cell-free DNA molecules. Each calibration data point specifies a gestational age corresponding to a calibration methylation level. The plurality of calibration samples may include, for example, plasma, serum, urine, saliva, cerebrospinal fluid, pleural fluid, amniotic fluid, peritoneal fluid, or ascitic fluid samples. For example, in some embodiments, the plurality of calibration samples includes maternal plasma samples from pregnant women during various stages of their pregnancies. For each calibration sample of the plurality of calibration samples, a methylation level of cell-free DNA molecules may be determined based on counts of DNA molecules methylated at one or more sites as described above.

At block 850, the measured methylation level of the biological sample may be compared to a calibration methylation level of at least one calibration data point. For example, the calibration methylation levels of the calibration data points may be plotted on a chart and form clusters for different gestational ages, and the measured methylation level of the biological sample may also be plotted on the chart to determine the cluster that the measured methylation level of the biological sample falls in.

At block 860, the gestational age of the fetus may be estimated based on the comparison. For example, the gestational age of the fetus may be determined as the gestational age associated with the cluster that the measured methylation level of the biological sample falls in.

In some implementations, the estimated gestational age may be compared with a gestational age determined using another technique for the biological sample, such as, for example, the gestational age determined based on the date of the last menstrual period (medical history) or based on ultrasonic diagnosis. An alarm message can be generated when the estimated gestational age does not match the gestational age determined using other techniques. The medical personnel may then determine whether the mismatch is caused by administrative errors (e.g., errors in medical history) or pathological reasons. A corrective action may be taken if the mismatch is caused by administrative errors. Further diagnosis may be conducted if the mismatch may be caused by pathological reasons, for example, pregnancy-associated disorders, such as preeclampsia, preterm labor, intrauterine growth restriction (IUGR), fetal chromosomal aneuploidies, etc.

In some embodiments, additionally or alternatively, a statistical value based on counts of cell-free DNA fragments corresponding to various sizes may be measured or calculated and used to determine the gestational age of a biological sample, alone or in combination with the methylation level, as described above with respect to FIG. 7. As described above, a size distribution of cell-free DNA fragments can be determined using, for example but not limited to, real-time PCR, targeted enrichment, electrophoresis, and mass spectrometry analysis. The size of a DNA fragment can be represented by a length, a molecular mass, or a measured parameter that is proportional to the length or mass, such as the mobility in a electrophoretogram and the time required to travel a fixed distance in electrophoresis or mass spectrometer. The proportions (or frequencies) of fetal-specific or all cell-free DNA fragments of different sizes in each reference sample may be plotted as shown in, for example, FIGS. 1, 2A, and 2B.

In some embodiments, the statistical value may include the proportion of (fetal-specific) cell-free DNA fragments with sizes greater than, for example, about 150 bp or other suitable values, which may be the cumulative frequency of fetal-specific or all cell-free DNA fragments greater than 150 bp. In some embodiments, the statistical value may include the proportion of fetal-specific or all cell-free DNA fragments with a size no greater than, for example, about 150 bp or other suitable values. Similar statistical values may be measured or calculated using calibration samples to determine calibration statistical values. The correlation between gestational ages and the statistical values and/or the methylation level may be stored in the calibration data points, and may be used to determine the gestational age associated with a sample by comparing the measured statistical value (and/or the measured methylation level) for the sample to a calibration statistical value (and/or) a calibration methylation level.

It is noted that even though FIG. 8 describes the method as sequential processes, many of the operations can be performed in parallel or concurrently. In addition, the order of the operations may be rearranged. An operation may have additional steps not included in the figure. Some operations may be optional, and thus may be omitted in various embodiments. Some operations described in one block may be performed together with operations at another block. Some operations may be performed repeatedly or reiteratively. For example, results from the biological sample may be used to analyze a new biological sample. Furthermore, embodiments of the methods may be implemented in hardware, software, firmware, middleware, microcode, hardware description languages, or any combination thereof.

V. Ending Position Analysis

High molecular weight genomic tissue DNA fragments that are sheared or sonicated in vitro show DNA molecules with ending positions randomly scattered across the genome. However, the study of the actual ending positions or termini of individual cell-free DNA molecules, especially plasma DNA molecules, shows that the locations where cell-free DNA molecules are cut are not random. The process of cell-free DNA fragmentation may be orchestrated down to the specific nucleotide position of cutting or cleavage. There are certain ending positions of cell-free DNA molecules that are highly represented within a sample, such as plasma. The number of occurrences or representations of such ending positions is statistically significantly higher than expected by chance alone. These non-random positions of cell-free DNA ending positions may be referred to as the preferred ending positions or preferred ends.

In some case, there are cell-free DNA ending positions that commonly occur (i.e., preferred ends) across individuals of various physiological states or disease states. For example, there are preferred ends that mostly occur in pregnant women. These pregnancy-specific ends are also highly represented in other individuals with comparable physiological state. For example, preferred ends identified in the plasma of one pregnant woman may also be detected in the plasma of other pregnant women. Furthermore, the proportions of cell-free DNA fragments with such preferred ends in a sample from a pregnant woman correlates with the fetal DNA fraction in the plasma of the pregnant woman. Such preferred ends are determined to be associated with the pregnancy or the fetus because their quantities reduce substantially in the post-delivery maternal plasma samples.

There are a number of applications or utilities for the analysis of cell-free DNA preferred ends. They could provide information about the fetal DNA fraction in pregnancy and hence the health of the fetus. For example, a number of pregnancy-associated disorders, such as preeclampsia, preterm labor, intrauterine growth restriction (IUGR), fetal chromosomal aneuploidies and others, have been reported to be associated with perturbations in the fractional concentration of fetal DNA, namely fetal DNA fraction, or fetal fraction, compared with gestational age-matched control pregnancies.

A. Determination of Ending Position

A catalog of preferred ends relevant to particular physiological states or pathological states can be identified by comparing the cell-free DNA profiles of preferred ends among individuals with different physiological states, e.g., non-pregnant compared with pregnant samples. Another approach is to compare the cell-free DNA profiles of preferred ends at different times of a physiological (e.g., pregnancy) process. Examples of such time points include before and after pregnancy.

In some embodiments, the preferred ends could be identified using genetic markers that are relevant for a particular tissue. For example, cell-free DNA molecules containing a fetal-specific SNP allele could be useful for identifying fetal-specific preferred ends in a sample such as maternal plasma. Similarly, plasma DNA molecules containing a maternal-specific SNP allele would be useful for identifying maternal-specific preferred ends in maternal plasma.

A preferred end can be considered relevant for a physiological state when it has a high likelihood or probability of being detected in that physiological state. In some embodiments, a preferred end is of a certain probability more likely to be detected in the relevant physiological state than in other states. Because the probability of detecting a preferred end in a relevant physiological state is higher, such preferred or recurrent ends (or ending positions) could be seen in more than one individual with the same physiological state. The high probability could also render such preferred or recurrent ends to be detectable many times in the same cell-free DNA sample or aliquot of the same individual. In some embodiments, a quantitative threshold may be set to only include ends that are detected at least a specified number of times (e.g., 5, 10, 15, 20, etc.) within the same sample or same sample aliquot in the preferred ends.

After a catalog of cell-free DNA preferred ends is established for any physiological or pathological state, targeted or non-targeted methods could be used to detect their presence in cell-free DNA samples, such as plasma, of other individuals to determine a classification of the other individuals. For example, the cell-free DNA preferred ends could be detected by random non-targeted sequencing. The sequencing depth would need to be considered so that a reasonable probability of identifying all or a portion of the relevant preferred ends could be achieved. Alternatively, hybridization capture of loci with high density of preferred ends could be performed on the cell-free DNA samples to enrich the sample with cell-free DNA molecules with such preferred ends following, for example, but not limited to, detection by sequencing, microarray, or the PCR. Amplification based approaches could also be used to specifically amplify and enrich the cell-free DNA molecules with the preferred ends, such as inverse PCR or rolling circle amplification. The amplification products could be identified by sequencing, microarray, fluorescent probes, gel electrophoresis, or other standard approaches known to those skilled in the art.

B. Example Results

There might be sites in the maternal and fetal genomes that would be preferentially cleaved in the generation of plasma DNA. Preferred ending positions of fetal-specific cell-free DNA fragments can be obtained by analyzing a plasma DNA from a pregnant woman. The fetal- and maternal-derived plasma DNA fragments can be differentiated through polymorphism-based methods. Fragments carrying fetal- and maternal-specific alleles (informative SNPs) can then be used for determining the preferred ending positions of the fetal-derived and maternal-derived DNA.

Figures 9A, 9B:
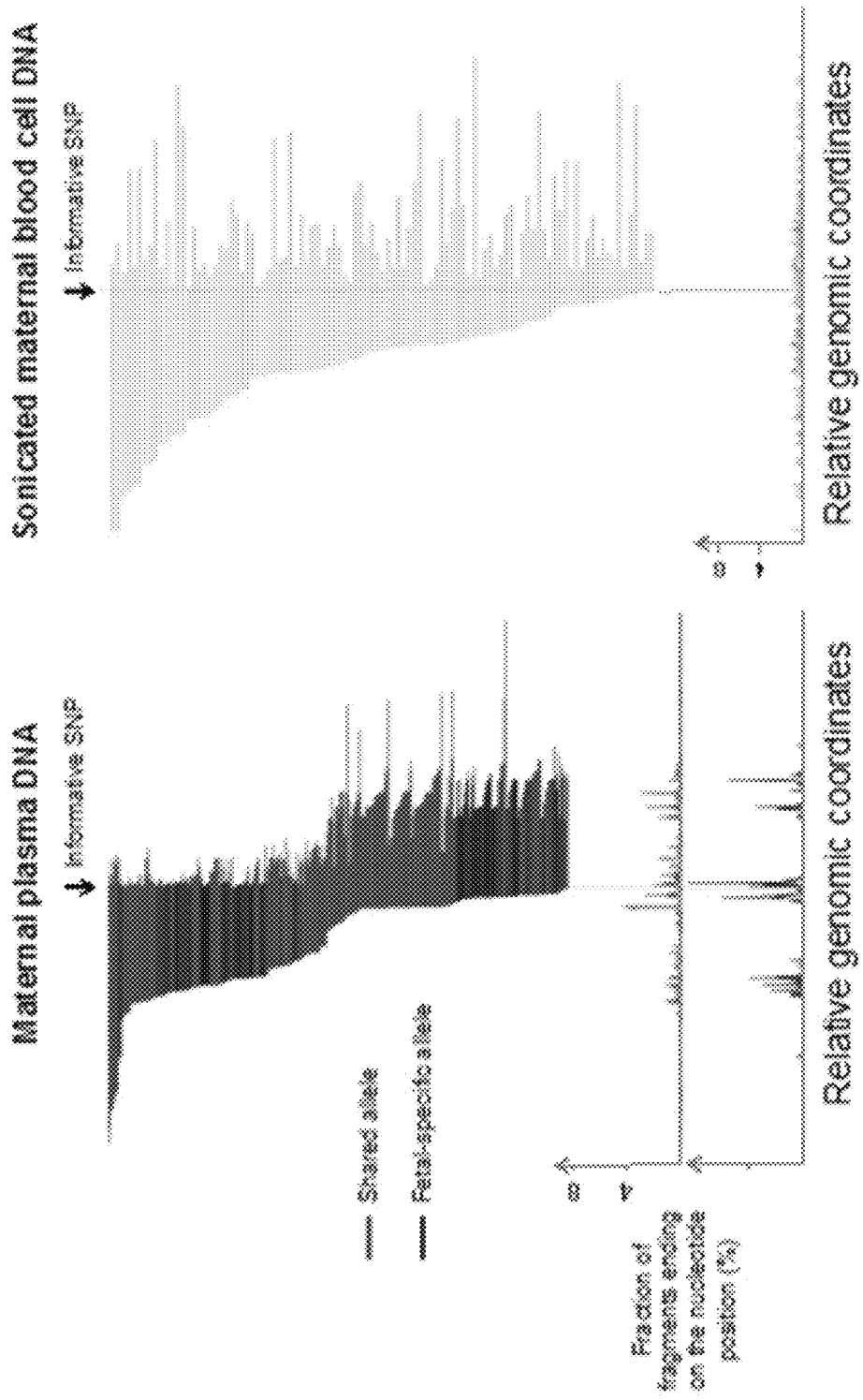
FIG. 9A shows an illustrative example of non-random fragmentation patterns of plasma DNA carrying a fetal-specific allele and an allele shared by the mother and the fetus, according to certain embodiments of the present invention.
FIG. 9B shows example sequencing results of a DNA sample obtained from blood cells and artificially fragmented using sonication, according to certain embodiments of the present invention.

FIG. 9A shows an illustrative example of non-random fragmentation patterns of plasma DNA carrying a fetal-specific allele and an allele shared by the mother and the fetus, according to certain embodiments of the present invention. FIG. 9B shows sequencing results of a DNA sample obtained from blood cells and artificially fragmented using sonication as a control, according to certain embodiments of the present invention. On the upper part of FIGS. 9A and 9B, each horizontal line represents one sequenced DNA fragment. The ends of the DNA fragments represent the ending position of the sequenced DNA fragments. The fragments are sorted according to the coordinate of the left outermost nucleotide (smallest genomic coordinate). On the lower part of FIGS. 9A and 9B, the percentage of DNA fragments ending on a particular position is shown. The horizontal axis on the lower parts of FIGS. 9A and 9B represents the genomic coordinates and the informative SNP is located at the center indicated by the dotted line.

As shown in FIG. 9A, a non-random fragmentation ending pattern is observed in the plasma DNA. In the plot of the probability of fragments ending on specific nucleotide position, three peaks are observed for each of the two groups of fragments carrying the fetal-specific alleles and alleles shared by the mother and the fetus. These peaks represent the hotspots for the end positions of fetal- and maternal-derived DNA in maternal plasma, respectively. The positions of the peaks largely overlapped between fetal-derived DNA fragments and maternal-derived DNA fragments. In contrast, the fragmentation pattern for the sonicated DNA from a blood cell shown in FIG. 9B appears to be random and the probability of fragment ending on a nucleotide position is similar across the region.

A p-value may be calculated to determine if a particular position has significantly increased probability of being an end for the reads carrying the shared allele or the fetal-specific allele based on Poisson probability function:

$$p\text{-value}=\text{Poisson}(N_{actual}, N_{predict}),$$

where Poisson( ) is the Poisson probability function, $N_{actual}$ is the actual number of reads ending at the particular nucleotide, and $N_{predict}$ is the total number of reads divided by the mode value of the size of cell-free DNAs (e.g., 166 bp). A p-value of <0.01 is used as a cutoff to define preferred ending positions for the reads carrying the fetal-specific allele or the shared allele. Statistically significant ending positions are determined for DNA fragments carrying the shared allele and the fetal-specific allele independently. Other probability distributions can be used, e.g., binomial distribution, negative binomial distribution, and normal distribution.

Figure 10:
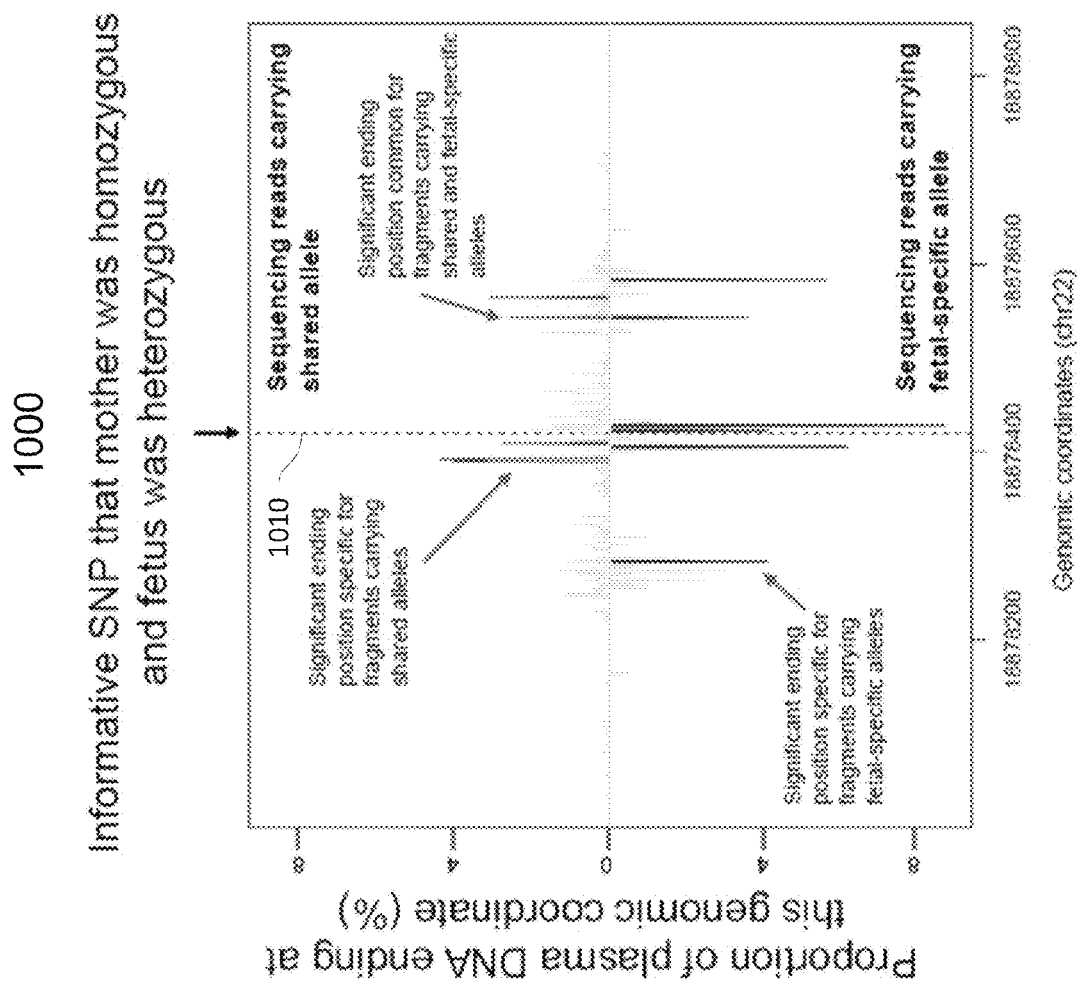
FIG. 10 shows a plot of the probability a genomic coordinate being an ending position of maternal plasma DNA fragments across a region with an informative SNP, according to certain embodiments of the present invention.

FIG. 10 shows a plot 1000 of the probability a genomic coordinate being an ending position of maternal plasma DNA fragments across a region with an informative SNP, according to certain embodiments of the present invention. Results for nucleotide positions with a significantly increased probability of being an end of plasma DNA fragments carrying a shared allele and a fetal-specific allele are shown in the top and bottom parts of FIG. 10, respectively. The horizontal axis represents the genomic coordinates and the mutation (informative SNP) is located at the center indicated by a dotted line 1010. As shown, there are coordinates that have a high rate of occurrence of at the ending positions for just fragments carrying the fetal-specific allele, for just fragments carrying the shared allele, or for fragments carrying both.

C. Relationship between Ending Patterns and Gestational Ages

As described above, the fragmentation ending pattern of plasma DNA has been demonstrated to follow non-random distribution (Lo Y M et al. Sci Transl Med. 2010:61ra91; Snyder M W et al. Cell. 2016; 164:57-68; Strayer R et al. Prenat Diagn. 2016; 36:614-21; Maxim I et al. BMC Genomics. 2015; 16:S1). The fragmentation ending pattern of maternal plasma DNA may also correlate with gestational age. Thus, the DNA ending pattern in maternal plasma may also provide an estimation of the gestational age of pregnancies as shown by the results of a study below.

In the study, plasma DNA samples are obtained from 57 and 11 women pregnant with male fetuses at the first and third trimesters, respectively. Each plasma DNA sample is subjected to massively parallel paired-end sequencing (e.g., using Illumina HiSeq2500). To achieve high-depth sequencing coverage, 1st- and 3rd-trimester sequencing results are pooled to form three representative 1st-trimester pools (with mean sequencing depth of 93×) and three representative 3rd-trimester pools (with mean sequencing depth of 21×), respectively. One 3rd-trimester pregnant woman carrying a male fetus is sequenced without pooling to ~270×haploid genome coverages. The data from this sample is used to define the most prevalent 0.5% end sites on Y chromosome that would be present in maternal plasma. These ends form the reference data set. The frequencies of recovering any of these most prevalent 0.5% plasma DNA end sites (i.e. the reference data set) in the maternal plasma DNA pools are then determined. In general, about 50 K most prevalent end sites are investigated per pool. The recovered ends are used to perform principal component analysis. Other classification techniques, including but not limited to linear discriminant analysis, logistic regression, machine learning algorithms, support vector machine, artificial neural network, k-means clustering, K-nearest neighbors, and random decision forests, may also be used. It is noted that, although Y chromosomes are used in the study, other chromosomes may be used, as long as the chromosomes include fetal-specific alleles.

Figure 11:
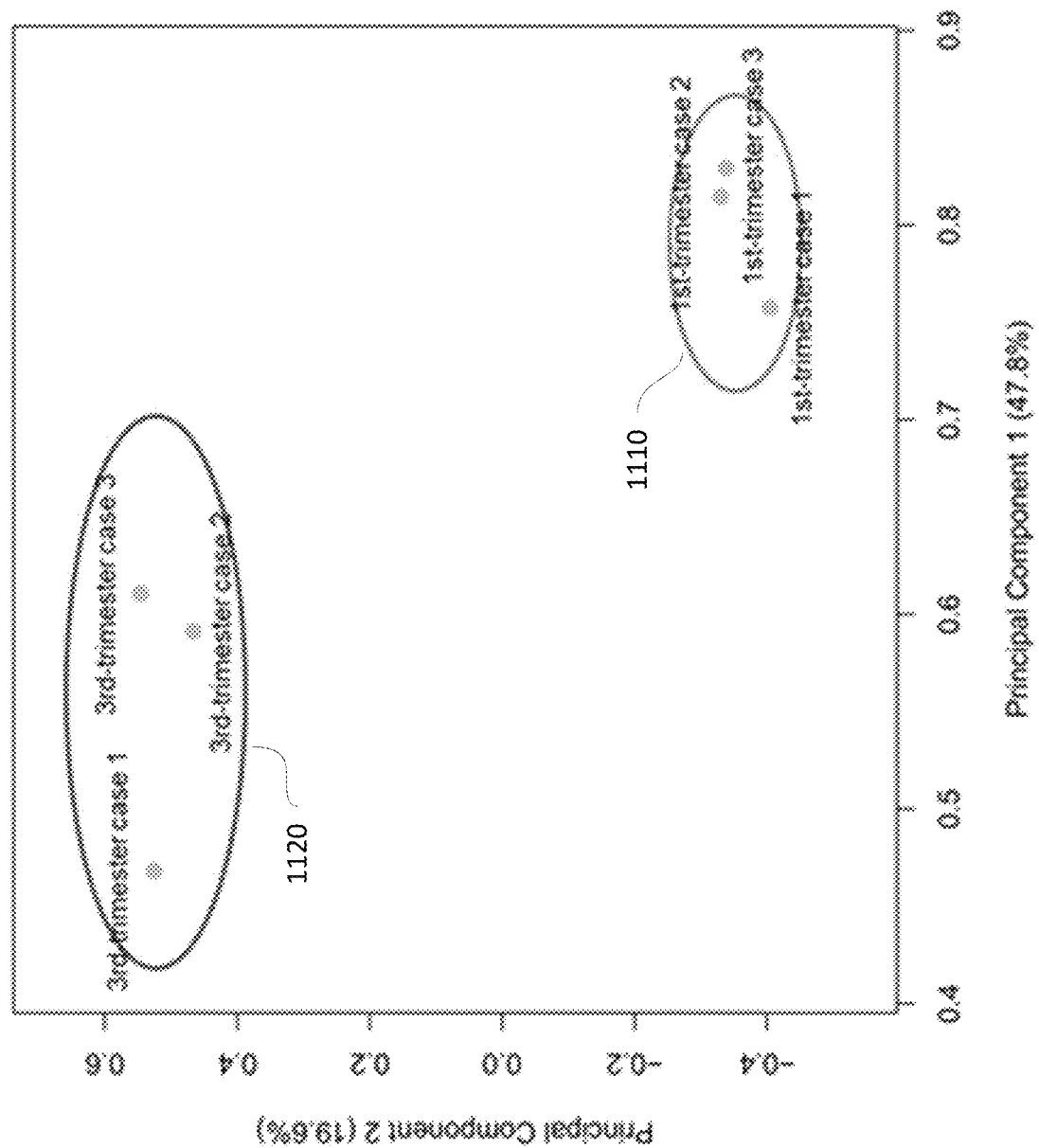
FIG. 11 illustrates the results of a principal component analysis of plasma DNA ending positions across samples with different gestational ages, according to certain embodiments of the present invention.

FIG. 11 illustrates example results of principal component analysis of plasma DNA ending positions across samples corresponding to different gestational ages, according to certain embodiments of the present invention. The normalized end frequencies for the most prevalent 0.5% (about 50 K) plasma DNA end sites ranked based on the frequencies that the plasma DNA molecules end on each end site are used to perform a principal component analysis. In FIG. 11, the horizontal axis represents the first principal component, where the value of the principal component for each sample is obtained by multiplying the frequencies that the plasma DNA molecules end on each end site of the 50 K most prevalent end sites with a first 50 K-dimensional vector that can provide the highest variance after the multiplication (linear transformation of the frequencies).

The results of the principal component analysis shows that, after such linear transformation using the first vector, 47.8% of the original variance may be captured. The vertical axis represents the second principal component, where the value of the second principal component for each sample is obtained by multiplying the frequencies that the plasma DNA molecules end on each end site of the 50 K most prevalent end sites with a second 50 K-dimensional vector, where the second vector has no correlation with the first vector, and the second highest variance can be achieved after the linear transformation using the second vector. The analysis results show that, using the second vector, about 19.6% of the original variance can be captured after the linear transformation. As shown in FIG. 11, the first and the third trimester samples form two distinct clusters: a cluster 1110 for the first trimester samples and a cluster 1120 for the third trimester samples. These data suggest that plasma DNA end patterns can be used for predicting gestational ages.

It is noted that even though FIG. 11 only shows clusters with respect to the first and third trimesters, those skilled in the art would understand that the data may be clustered using different time resolutions, such as by weeks, by bi-weeks, or by months during the pregnancy. Furthermore, more than two principal components can be used for the principal component analysis. In addition, in various embodiments, more or less most prevalent end sites, such as 1% or more end sites or 0.25% or less end sites, may be used. In various embodiments, the most prevalent end sites may be determined using one or more samples at different pregnancy stages, such as the first trimester, the second trimester, and/or the third trimester.

D. Example Method

Figure 12:
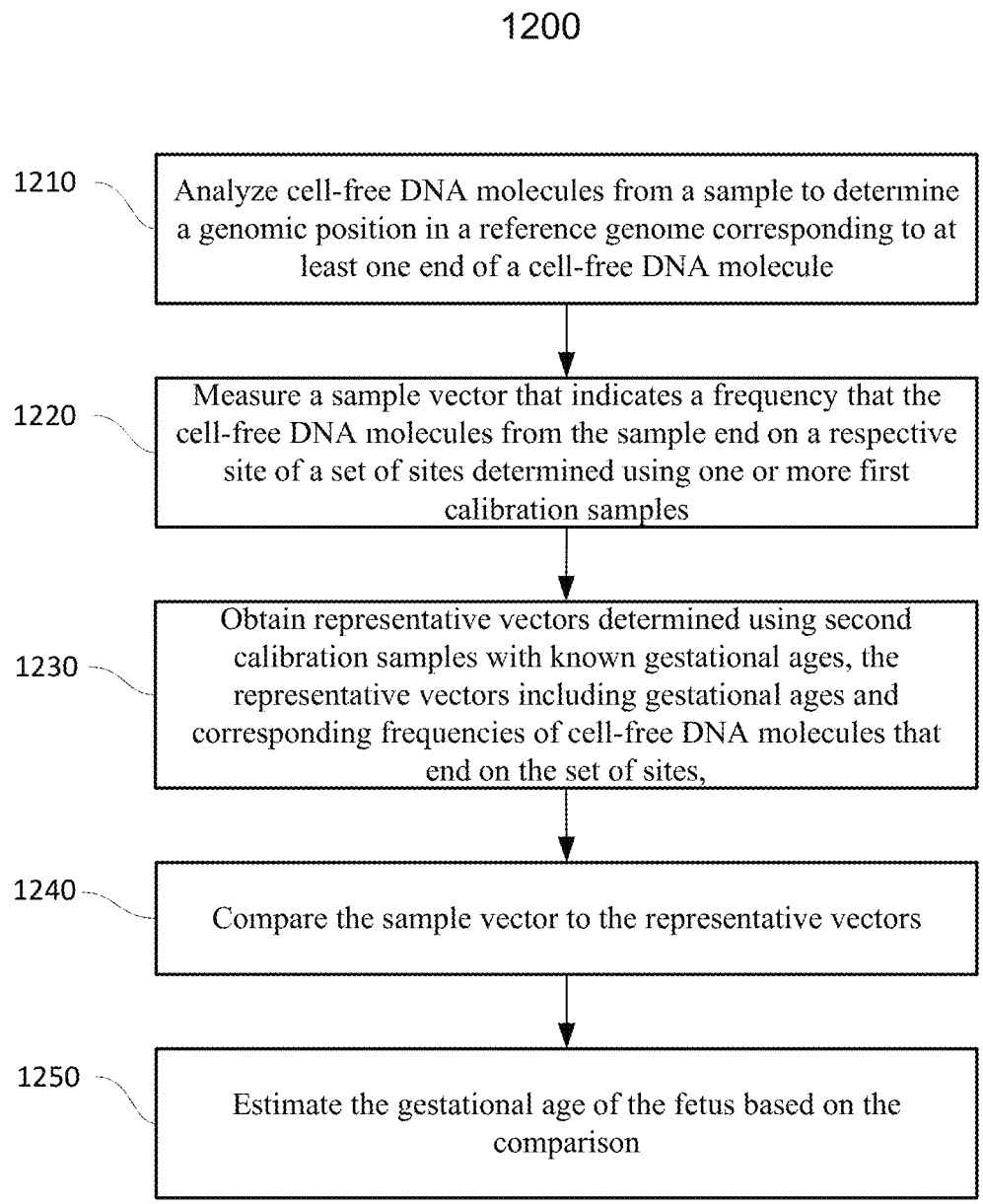
FIG. 12 is a flow chart illustrating an example method of determining the gestational age of a fetus based on an ending position analysis, according to certain embodiments of the present invention.

FIG. 12 is a flow chart illustrating an example method of determining gestational age of a fetus based on ending position analysis, according to certain embodiments of the present invention.

At block 1210, cell-free DNA molecules from a biological sample may be analyzed, where each cell-free DNA molecule may be analyzed by determining a genomic position in a reference genome corresponding to at least one end of the cell-free DNA molecule. The biological sample may include cell-free DNA molecules from a female subject and a fetus. The biological sample may be, for example, a plasma, serum, urine, saliva, cerebrospinal fluid, pleural fluid, amniotic fluid, peritoneal fluid, or ascitic fluid sample. For example, in some embodiments, the biological sample may include a maternal plasma sample from a pregnant woman. As described above, the ending positions of cell-free DNA molecules may be determined using targeted or non-targeted methods. In some embodiments, fetal DNA molecules, rather than all cell-free DNA molecules, may be identified and analyzed. For example, a fetal-specific allele may be identified by analyzing a maternal plasma sample from a pregnant woman and comparing detected alleles to alleles detected in a maternal-only sample, and the fetal-specific allele may be used for identifying fetal-specific cell-free DNA molecules (i.e., fetal DNA molecules).

At block 1220, a sample vector may be measured. Each value of the sample vector corresponds to a frequency that the cell-free DNA molecules end on a respective site of a set of sites. The set of sites may include the most prevalent sites (e.g., top 0.5% of all ending sites) determined based on numbers of cell-free DNA molecules that end on various sites in one or more first calibration samples. The frequency that the cell-free DNA molecules end on a respective site may be determined based on the total count of cell DNA molecules and the count of cell-free DNA molecules ending on the respective site. In some embodiments, one can use size or methylation to enrich fetal DNA molecules in a sample and profile the end sites of fetal DNA molecules using the cell-free DNA molecules in the enriched sample.

At block 1230, a plurality of representative vectors may be determined from one or more second calibration samples with known gestational ages, where each representative vector corresponds to a gestational age and includes representative frequencies that the cell-free DNA molecules end on the set of sites. The second calibration samples may include samples from a plurality of pregnant women at different pregnancy stages, such as the first trimester, second trimester, and third trimester. In some examples, a representative vector may be measured from a second calibration sample as described above with respect to the sample vector. In some example, a representative vector may be a centroid of a cluster of vectors measured from two or more calibration samples having a particular gestational age, where the centroid may be determined using an average of the vectors measured from the two or more calibration samples having the particular gestational age. In some example, the representative vectors may be determined using principal component analysis, which may provide eigenvectors associated with the largest eigenvalues of a covariance matrix.

At block 1240, the sample vector may be compared to the plurality of representative vectors to determine which representative vector is the closest to the sample vector. For example, the Euclidian distance between the sample vector and each representative vector may be calculated, and the representative vector that has the shortest Euclidian distance from the sample vector may be the closest representative vector. In other examples, the sample vector and the plurality of representative vectors may be analyzed using two or more dimensional principal component analysis as described with respect to FIG. 11 to find the representative vector closest to the sample vector.

At block 1250, a gestational age associated with the biological sample may be determined based on the gestational age associated with the closest representative vector. In some embodiments, the determined gestational age may be compared with a gestational age estimated using another technique for the biological sample, such as, for example, the gestational age determined based on the date of the last menstrual period (medical history) or based on ultrasonic diagnosis. An alarm message can be generated when the determined gestational age does not match the gestational age determined using other techniques. The medical personnel may then determine whether the mismatch is caused by administrative errors (e.g., errors in medical history) or pathological reasons. A corrective action may be taken if the mismatch is caused by administrative errors. Further diagnosis may be conducted if the mismatch may be caused by pathological reasons, for example, pregnancy-associated disorders, such as preeclampsia, preterm labor, intrauterine growth restriction, fetal chromosomal aneuploidies, etc.

It is noted that even though FIG. 12 describes the method as sequential processes, many of the operations can be performed in parallel or concurrently. In addition, the order of the operations may be rearranged. An operation may have additional steps not included in the figure. Some operations may be optional, and thus may be omitted in various embodiments. Some operations described in one block may be performed together with operations at another block. Some operations may be performed repeatedly or reiteratively. For example, results from the biological sample may also be used to analyze a new biological sample. Furthermore, embodiments of the methods may be implemented in hardware, software, firmware, middleware, microcode, hardware description languages, or any combination thereof.

In addition, in various embodiments, the method described in FIG. 12 may be used alone or in combination with other methods, such as the method described in FIG. 8, to more accurately and more reliably determine the gestational age of a fetus.

VI. Example Applications and Treatment

The gestational age determined using techniques disclosed herein may be referred to as biological (or molecular) gestational age in contrast to gestational age determined using other methods, such as gestational age determined based on the date of the last menstrual period (medical history-based gestational age) or based on ultrasonic diagnosis. The biological gestational age may be compared with the gestational age determined using other method, such as the medical history-based gestational age, for example, for cross-verification.

The result of the comparison may be used in various applications. For example, if the biological gestational age matches the medical-history-based gestational age, this may confirm that the determined gestational age is correct and that the fetus is developing as expected. On the other hand, if the two do not match, an alarm may be generated. In some cases, the alarm may alert administrative personnel to check if the mismatch is caused by administrative errors regarding the medical history.

If it is determined that no administrative error is made, the mismatch may be caused by pathological reasons. In some cases, the biological gestational age may be older than the gestational age based on the last menstrual period, which may help to avoid incorrectly interpreting the commencement of labor as a preterm delivery at a later stage of pregnancy. True preterm delivery may require a corticosteroid therapy to improve fetal lung maturity. The avoidance of the misinterpretation of preterm delivery may thus avoid an unnecessary corticosteroid therapy. On the other hand, if there is no sign of labor at a true biological gestational age of 42 months, uterine stimulants (e.g. oxytocin) may need to be administered. In contrast, if the biological gestational age estimated by the molecular methods disclosed herein is younger than the gestational age determined based on the last menstrual period, one may need to be vigilant regarding when a delivery would be considered a preterm delivery that would warrant a corticosteroid therapy, or may need not to mislabel a pregnancy as having no sign of labor after 42 weeks and requiring uterine stimulants. In some cases, the biological gestational age may be older than the gestational age estimated using ultrasound. This may indicate intrauterine fetal growth retardation. Such an observation may trigger a more intensive antenatal regimen, such as more regular ultrasound assessment, or assessment and monitoring for preeclampsia and preterm labor. If the risk of preeclampsia is deemed to be high, an aspirin therapy may be given to the patient to reduce the risk of preeclampsia. On the other hand, if the biological gestational age is younger than the gestational age estimated using ultrasound, macrosomia of the fetus may be diagnosed, which may require earlier induction of labor. Thus, the biological gestational age may be used to monitor the progress of gestation and determine whether the biological gestational progress is faster or slower than normal. In addition, the biological gestational age may be affected by certain diseases. Thus, the mismatch between the biological gestational age and the gestational age determined by other method may indicate a potential disease in the fetus, for example, pregnancy-associated disorders, such as preeclampsia, preterm labor, IUGR, fetal chromosomal aneuploidies, etc.

Once detected to have one or more potential diseases in the fetus, the mother can be administered a compound to treat the potential diseases. A therapeutic agent for the treatment may be incorporated into compositions, which in some embodiments are suitable for pharmaceutical use. Such compositions may comprise the peptide or polypeptide, and an acceptable carrier, for example one that is pharmaceutically acceptable. A "pharmaceutically acceptable carrier" includes any and all solvents, dispersion media, coatings, antibacterial and antifungal agents, isotonic and absorption delaying agents, and the like, compatible with pharmaceutical administration. Examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions. A therapeutic agent (and any additional therapeutic agent for the treatment) can be administered by any suitable means, including parenteral, intrapulmonary, intrathecal and intranasal, and, if desired for local treatment, intralesional administration. Parenteral infusions include, e.g., intramuscular, intravenous, intra-arterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various timepoints, bolus administration, and pulse infusion are contemplated herein.

The route of administration of a therapeutic agent can be oral, intraperitoneal, transdermal, subcutaneous, by intravenous or intramuscular injection, by inhalation, topical, intralesional, infusion, liposome-mediated delivery, topical, intrathecal, gingival pocket, rectal, intrabronchial, nasal, transmucosal, intestinal, ocular or otic delivery, or any other methods known in the art. In some embodiments, the therapeutic agent is administered orally, intravenously, or intraperitoneally. In some embodiments, the therapeutic agent is administered at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is within the capability of those skilled in the art.

In some embodiments, a therapeutic agent is administered to the subject over an extended period of time, for example, for at least 30, 40, 50, 60, 70, 80, 90, 100, 150, 200, 250, 300, 350 day or longer.

VII. Example System

Figure 13:
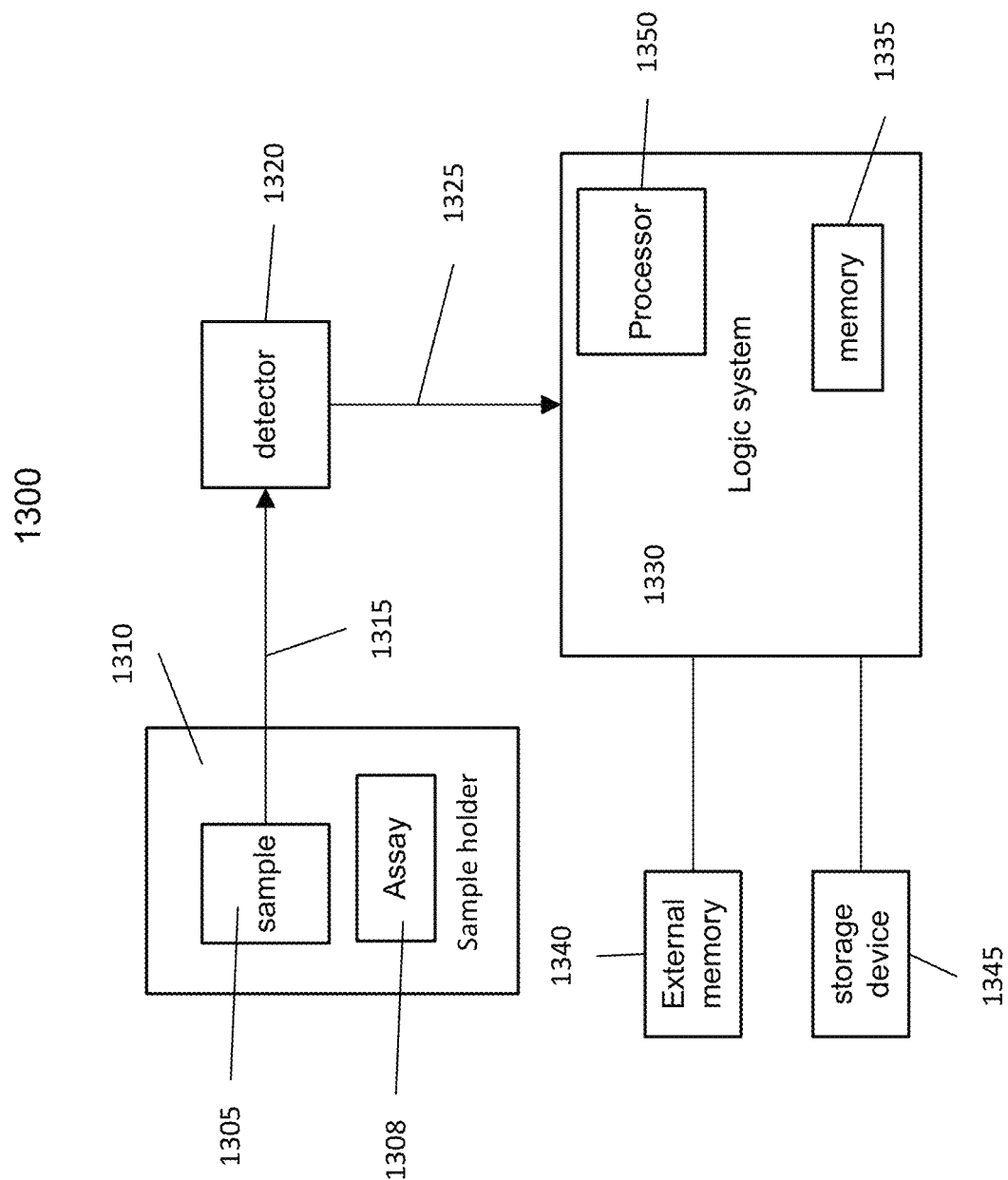
FIG. 13 illustrates a system according to an embodiment of the present invention.

FIG. 13 illustrates a system 1300 according to an embodiment of the present invention. The system as shown includes a sample 1305, such as cell-free DNA molecules within a sample holder 1310, where sample 1305 can be contacted with an assay 1308 to provide a signal of a physical characteristic 1315. An example of a sample holder can be a flow cell that includes probes and/or primers of an assay or a tube through which a droplet moves (with the droplet including the assay). Physical characteristic 1315, such as a fluorescence intensity value, from the sample is detected by detector 1320. Detector can take a measurement at intervals (e.g., periodic intervals) to obtain data points that make up a data signal. In one embodiment, an analog to digital converter converts an analog signal from the detector into digital form at a plurality of times. A data signal 1325 is sent from detector 1320 to logic system 1330. Data signal 1325 may be stored in a local memory 1335, an external memory 1340, or a storage device 1345.

Logic system 1330 may be, or may include, a computer system, ASIC, microprocessor, etc. It may also include or be coupled with a display (e.g., monitor, LED display, etc.) and a user input device (e.g., mouse, keyboard, buttons, etc.). Logic system 1330 and the other components may be part of a stand-alone or network connected computer system, or they may be directly attached to or incorporated in a thermal cycler device. Logic system 1330 may also include optimization software that executes in a processor 1350. Logic system 1330 may include a computer readable medium storing instructions for controlling system 1300 to perform any of the methods described herein.

Figure 14:
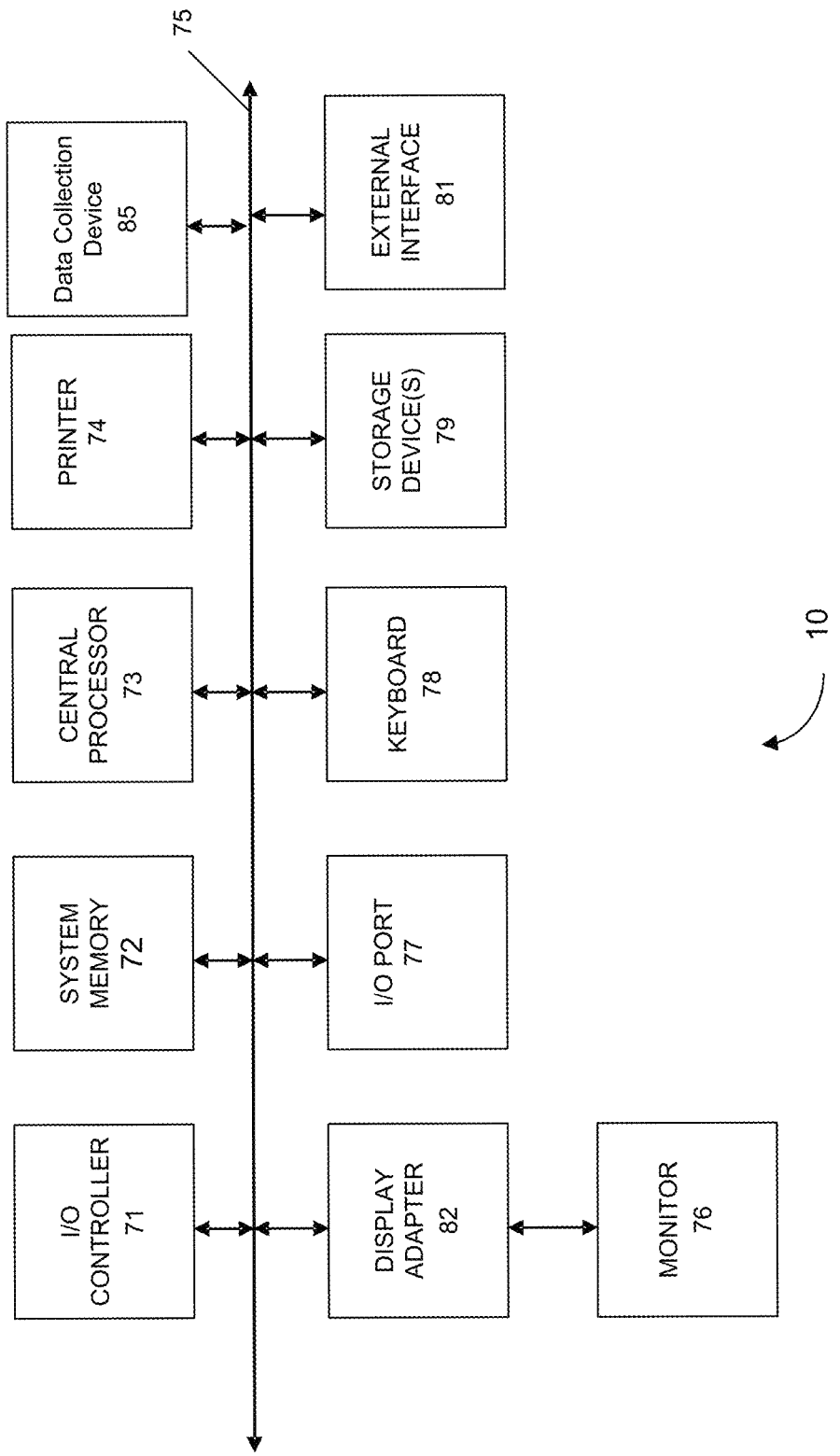
FIG. 14 shows a block diagram of an example computer system usable with system and methods according to certain embodiments of the present invention.

Any of the computer systems mentioned herein may utilize any suitable number of subsystems. Examples of such subsystems are shown in FIG. 14 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 14 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of connections known in the art such as input/output (I/O) port 77 (e.g., USB, FireWire®). For example, I/O port 77 or external interface 81 (e.g., Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g., an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g., a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A method of analyzing a biological sample from a female subject pregnant with a fetus, the biological sample including cell-free DNA molecules from the female subject and the fetus, the method comprising:
   receiving the biological sample;
   analyzing the cell-free DNA molecules from the biological sample, wherein analyzing a cell-free DNA molecule includes:
      determining a location of the cell-free DNA molecule in a genome, the genome being a genome of the fetus or the female subject; and
      determining whether the cell-free DNA molecule is methylated at one or more sites of a plurality of sites, wherein the analyzing includes performing massively parallel sequencing of cell-free DNA molecules in the biological sample to obtain sequence reads;
   for each of the plurality of sites:
      determining, by a computer system, a respective number of cell-free DNA molecules that are methylated at the site using the sequence reads;
   determining, by the computer system, a measured methylation level of cell-free DNA molecules in the biological sample based on the respective numbers of cell-free DNA molecules methylated at the plurality of sites as determined using the sequence reads;
   obtaining, by the computer system, one or more calibration data points, wherein each calibration data point specifies a gestational age corresponding to a calibration methylation level of cell-free DNA molecules, and wherein the one or more calibration data points are determined from a plurality of calibration samples with known gestational ages;
   comparing, by the computer system, the measured methylation level to a calibration methylation level of at least one calibration data point;
   estimating, by the computer system, a gestational age of the fetus based on the comparing;
   determining that the estimated gestational age does not match another gestational age determined using another technique; and
   in response to determining that the estimated gestational age does not match the other gestational age determined using the other technique, generating an alarm message.

2. The method of claim 1, wherein the other technique includes an ultrasound-based method or a last menstrual period-based method.

3. The method of claim 1, further comprising:
   administering a treatment in response to the alarm message according to a determined pathological cause of a mismatch between the estimated gestational age and the other gestational age determined using the other technique.

4. The method of claim 3, wherein the treatment includes a treatment for at least one of preeclampsia, preterm labor, intrauterine growth restriction (IUGR), or fetal chromosomal aneuploidies.

5. The method of claim 1, further comprising identifying a plurality of fetal cell-free DNA molecules from the biological sample, each fetal cell-free DNA molecule having a fetal-specific allele.

6. The method of claim 1, wherein determining the measured methylation level of cell-free DNA molecules in the biological sample is based on a fraction of fetal DNA molecules in the biological sample.

7. The method of claim 1, further comprising:
   determining a measured statistical value based on counts of cell-free DNA molecules corresponding to various sizes in the biological sample, wherein each calibration data point of the one or more calibration data points specifies the gestational age corresponding to (1) the calibration methylation level and (2) and a calibration statistical value determined using the plurality of calibration samples, wherein comparing the measured methylation level to the calibration methylation level of at least one calibration data point comprises comparing the measured methylation level and the measured statistical value to a calibration methylation level and a calibration statistical value of at least one calibration data point.

8. The method of claim 7, wherein the measured statistical value includes a proportion of cell-free DNA molecules with a size greater than or less than a threshold number of base pairs in the biological sample.

9. The method of claim 1, wherein the plurality of sites correspond to a plurality of CpG sites, and wherein the measured methylation level is determined by:

$$MD = \frac{M}{M+U},$$

wherein M is a count of cell-free DNA molecules methylated at the plurality of CpG sites and U is a count of cell-free DNA molecules unmethylated at the plurality of CpG sites.

10. The method of claim 1, wherein the plurality of calibration samples includes maternal plasma samples from pregnant female subjects at various pregnancy stages.

11. The method of claim 1, wherein the plurality of sites include at least 5,000 sites.

12. The method of claim 1, wherein determining whether the cell-free DNA molecule is methylated at the one or more sites of the plurality of sites includes performing bisulfate sequencing of the cell-free DNA molecule.

13. The method of claim 1, further comprising determining an estimated due date based on the estimated gestational age of the fetus.

14. The method of claim 1, wherein:
at each of one or more additional times:
receiving an additional biological sample from the female subject, wherein the additional biological sample includes cell-free DNA molecules from the female subject and the fetus; and
for the additional biological sample:
performing the steps of analyzing the cell-free DNA molecules, determining the respective number of cell-free DNA molecules, determining the measured methylation level, obtaining the one or more calibration data points, and comparing the measured methylation level to the calibration methylation level; and
estimating, by the computer system, a gestational age of the fetus based on the comparing of the measured methylation level to the calibration methylation level.

15. The method of claim 1, wherein the one or more calibration data points are determined by:
for each calibration sample of the plurality of calibration samples:
determining a calibration methylation level based on numbers of cell-free DNA molecules methylated at the plurality of sites; and
determining the one or more calibration data points based on the known gestational ages and the calibration methylation levels of the plurality of calibration samples.

16. A computer product comprising a non-transitory computer readable medium storing a plurality of instructions for controlling a computer system coupled to a sequencer to:
analyze cell-free DNA molecules from a biological sample from a female subject pregnant with a fetus, the biological sample including cell-free DNA molecules from the female subject and the fetus, wherein analyzing a cell-free DNA molecule includes:
determining a location of the cell-free DNA molecule in a reference genome; and
determining whether the cell-free DNA molecule is methylated at one or more sites of a plurality of sites, wherein the analyzing includes performing massively parallel sequencing of cell-free DNA molecules in the biological sample to obtain sequence reads;
determine, for each of the plurality of sites, a respective number of cell-free DNA molecules that are methylated at the site using the sequence reads;
determine a measured methylation level of cell-free DNA molecules in the biological sample based on the respective numbers of cell-free DNA molecules methylated at the plurality of sites as determined using the sequence reads;
obtain one or more calibration data points, wherein each calibration data point specifies a gestational age corresponding to a calibration methylation level of cell-free DNA molecules, and wherein the one or more calibration data points are measured from a plurality of calibration samples with known gestational ages;
compare the measured methylation level to a calibration methylation level of at least one calibration data point;
estimate a gestational age of the fetus based on the comparing;
determine that the estimated gestational age does not match another gestational age determined using another technique; and
in response to determining that the estimated gestational age does not match the other gestational age determined using the other technique, generate an alarm message.

17. The computer product of claim 16, wherein the plurality of instructions further includes instructions for controlling the computer system to:
determine a measured statistical value based on counts of cell-free DNA molecules corresponding to various sizes in the biological sample, wherein each calibration data point of the one or more calibration data points specifies the gestational age corresponding to (1) the calibration methylation level and (2) and a calibration statistical value determined using the plurality of calibration samples,
wherein comparing the measured methylation level to the calibration methylation level of at least one calibration data point comprises comparing the measured methylation level and the measured statistical value to a calibration methylation level and a calibration statistical value of at least one calibration data point.

18. The computer product of claim 16, wherein determining the measured methylation level of cell-free DNA molecules in the biological sample is based on a fraction of fetal DNA molecules in the biological sample.

19. A system comprising:
a detector configured to:
measure physical characteristics of a plurality of cell-free DNA molecules in a biological sample from a female subject pregnant with a fetus to perform massively parallel sequencing of cell-free DNA molecules in the biological sample to obtain data signals embodying sequence reads; and provide the data signals corresponding to the physical characteristics; and a logic system comprising one or more processors, memory, and an interface configured to receive the data signals, the logic system configured to use the data signals for:

analyzing the cell-free DNA molecules from the biological sample, wherein analyzing a cell-free DNA molecule includes:

determining a location of the cell-free DNA molecule in a reference genome; and determining whether the cell-free DNA molecule is methylated at one or more sites of a plurality of sites;

determining, for each of the plurality of sites, a respective number of cell-free DNA molecules that are methylated at the site using the sequence reads;

determining a measured methylation level of cell-free DNA molecules in the biological sample based on the respective numbers of cell-free DNA molecules methylated at the plurality of sites as determined using the sequence reads;

obtaining one or more calibration data points, wherein each calibration data point specifies a gestational age corresponding to a calibration methylation level of cell-free DNA molecules, and wherein the one or more calibration data points are measured from a plurality of calibration samples with known gestational ages;

comparing the measured methylation level to a calibration methylation level of at least one calibration data point;

estimating a gestational age of the fetus based on the comparing;

determining that the estimated gestational age does not match another gestational age determined using another technique; and in response to determining that the estimated gestational age does not match the other gestational age determined using the other technique, generating an alarm message.

20. The system of claim 19, wherein the logic system is further configured to use the data signals for:

determining a measured statistical value based on counts of cell-free DNA molecules corresponding to various sizes in the biological sample, wherein each calibration data point of the one or more calibration data points specifies the gestational age corresponding to (1) the calibration methylation level and (2) and a calibration statistical value determined using the plurality of calibration samples, wherein comparing the measured methylation level to the calibration methylation level of at least one calibration data point comprises comparing the measured methylation level and the measured statistical value to a calibration methylation level and a calibration statistical value of at least one calibration data point.

* * * * *